(12) United States Patent
Lang

(10) Patent No.: US 11,389,499 B2
(45) Date of Patent: Jul. 19, 2022

(54) HIGH FIBER NUTRITIONAL COMPOSITIONS WITH IMPROVED ORGANOLEPTIC CHARACTERISTICS FOR BETTER DIET MANAGEMENT

(71) Applicant: David Phillip Lang, Bristol, RI (US)

(72) Inventor: David Phillip Lang, Bristol, RI (US)

(73) Assignee: David Phillip Lang, Bristol, RI (US)

( * ) Notice: Subject to any disclaimer, the term of this patent is extended or adjusted under 35 U.S.C. 154(b) by 0 days.

(21) Appl. No.: 17/085,917

(22) Filed: Oct. 30, 2020

(65) Prior Publication Data

US 2021/0220421 A1 Jul. 22, 2021

Related U.S. Application Data

(60) Provisional application No. 62/964,640, filed on Jan. 22, 2020.

(51) Int. Cl.
| | |
|---|---|
| *A61K 36/68* | (2006.01) |
| *A61K 47/44* | (2017.01) |
| *A61K 47/46* | (2006.01) |
| *A61K 47/36* | (2006.01) |
| *A61K 9/107* | (2006.01) |
| *A23L 33/22* | (2016.01) |
| *A23L 33/115* | (2016.01) |
| *A23L 33/125* | (2016.01) |
| *A23L 29/10* | (2016.01) |
| *A23L 7/126* | (2016.01) |
| *A23G 1/40* | (2006.01) |
| *A23G 1/36* | (2006.01) |
| *A23L 33/00* | (2016.01) |

(52) U.S. Cl.
CPC ............ *A61K 36/68* (2013.01); *A23G 1/36* (2013.01); *A23G 1/40* (2013.01); *A23L 7/126* (2016.08); *A23L 29/10* (2016.08); *A23L 33/115* (2016.08); *A23L 33/125* (2016.08); *A23L 33/22* (2016.08); *A23L 33/40* (2016.08); *A61K 9/107* (2013.01); *A61K 47/36* (2013.01); *A61K 47/44* (2013.01); *A61K 47/46* (2013.01); *A23V 2002/00* (2013.01)

(58) Field of Classification Search
CPC ..................................................... A61K 36/68
See application file for complete search history.

(56) References Cited

U.S. PATENT DOCUMENTS

| 4,568,557 A | 2/1986 | Becker |
| 4,766,004 A | 8/1988 | Moskowitz |
| 6,569,445 B2 | 5/2003 | Manning |
| 7,115,297 B2 | 10/2006 | Stillman |
| 2002/0168448 A1 | 11/2002 | Mody |
| 2002/0197357 A1 | 12/2002 | Pfeiffer |
| 2005/0186306 A1 | 8/2005 | Sonneveld |
| 2005/0238694 A1 | 10/2005 | Gerhardt |
| 2005/0271600 A1 | 12/2005 | Coleman |
| 2010/0278981 A1 | 11/2010 | Ervin |
| 2011/0287134 A1 | 11/2011 | Ervin |

FOREIGN PATENT DOCUMENTS

| GB | 2319178 A | * 5/1998 | .......... A61K 36/068 |
| WO | 2007135126 | 11/2007 | |

OTHER PUBLICATIONS

Terenzi, Soy Lecithin in Chocolate: Why is it so Controversial?, web blog, Oct. 9, 2018, The Chocolate Journalist, web address: https://thechocolatejournalist.com/soy-lecithin-chocolate/.

Lang Pharma Nutrition, Inc, Choco-Fiber trademark registration (#86596588) certification documentation for CLASS 30: Chocolate-based ready-to-eat food bars, claimed first use in commerce of Aug. 6, 2018 (documentation inclusive of product labels) and associated withdrawal of the trademark application.

Easley et al., "The Modern Herbal Dispensatory", 2016 p. 59-61, https://books.google/com/books/about/The_Modern-HerbalDispensatory.html?d-NY2xCwAAQBAJ.

Taylor, "Advances in Food and Nutrition Research", vol. 55, 2008 Chapter 4, p. 195.

International Search Report and Written Opinion based on PCT/US2020/060480 dated Feb. 12, 2021.

* cited by examiner

*Primary Examiner* — Amy L Clark
(74) *Attorney, Agent, or Firm* — Transformative Legal, LLC; Len S. Smith; Denise M. Brown

(57) ABSTRACT

The present invention provides methods and compositions for supplementing dietary fiber intake through the administration of new psyllium-containing chocolate food products. The compositions can be used to supplement dietary fiber intake and promote dietary regulation and wellness management. The chocolate composition comprising particular ratios of chocolate, psyllium, and lipids, and the emulsion-forming formulation methods disclosed herein surprisingly reduce the unpleasant gelling in the mouth/throat during mastication/swallowing that is frequently associated with psyllium-containing products. The protective capabilities of the ingredients of the present compositions provide for and, accordingly, allow for, suitable manufacturing and improved organoleptic properties which promote long-term adoption and consistent use by subjects.

11 Claims, No Drawings

HIGH FIBER NUTRITIONAL COMPOSITIONS WITH IMPROVED ORGANOLEPTIC CHARACTERISTICS FOR BETTER DIET MANAGEMENT

CROSS-REFERENCE TO RELATED APPLICATIONS

This application claims the benefit of priority U.S. Provisional Patent Application 62/964,640, filed Jan. 22, 2020, the entirety of which is hereby incorporated by reference.

FIELD OF THE INVENTION

The current invention relates to psyllium-fiber-containing food products. More specifically, the invention relates to high-fiber-nutritional-supplement compositions, such as chocolate bars, comprising high amounts of psyllium fiber and having positive organoleptic properties for aiding in dietary matters; methods of producing such products; and uses of such products.

BACKGROUND OF THE INVENTION

The benefits of consuming dietary fiber are well known. Dietary fiber or "roughage" is derived from plant parts that the digestive system is unable to break down fully. As such, dietary fiber passes through the body and is excreted in a largely unchanged form.

There are two types of dietary fiber: soluble and insoluble fiber. Soluble fiber is dissolvable in water. As soluble fiber travels through the digestive system it typically absorbs water, forming a gel-like substance. As the fiber gel travels through the digestive tract, it binds and softens digestive waste making it easier to pass. The soluble dietary fiber gel also binds to glucose and cholesterol and slows or even prevents the absorption of these compounds into the bloodstream. Hence, the consumption of soluble fiber is linked to a lower risk of heart disease through the reduction of cholesterol and blood sugar levels. Soluble fiber is found in common foods, including oat bran, barley, beans, and peas.

Research has shown that the intake of both types of dietary fiber is imperative to a well-balanced and healthy diet. However, while the American Heart Association recommends that an average adult in the U.S. ingest 25-30 grams of total dietary fiber per day from food sources, the average adult typically only receives about 15 grams of fiber per day from food. Based on the cardiovascular and other health benefits arising from dietary fiber intake, e.g., reduction of risks of heart disease, stroke, obesity, type 2 diabetes, and related ailments, individuals are often advised to consume, or independently seek out for incorporation into their diet, fiber supplements for a quick, easy, and/or satisfying way to augment their daily fiber intake. Psyllium is one of the sources of fiber that has been approved by the US FDA as a dietary fiber for such purposes.

Psyllium is a type of soluble fiber material derived from the husk and seeds of the *Plantago ovata* plant. As a soluble fiber, psyllium promotes regularity by absorbing water, forming a sticky gel, and swelling, resulting in the formation of bulkier stools that are easier to pass. The soluble fiber of Psyllium forms a viscous gel, which is not absorbed by the small intestine. More specifically, psyllium mucilage (plant-derived gel) absorbs excess water while stimulating normal bowel elimination. Thus, psyllium can be considered a dietary fiber with bulk laxative properties and, accordingly, it is a product that is often used to avoid or treat constipation.

Psyllium also has been associated with a diet that aids in the maintenance of optimal health, and even the prevention and treatment of certain health conditions, including diarrhea, irritable bowel syndrome, heart disease/heart health, overeating/obesity (e.g., by acting as an appetite suppressant), type 2 diabetes (by, e.g., lowering glucose levels), and high blood cholesterol/hypercholesterolemia (by, e.g., blocking cholesterol absorption).

Psyllium has been used for thousands of years as a traditional health medicine and supplement, especially in India. In 1934 Metamucil® was introduced into the U.S. market by G. D. Searle & Company, which marketed Metamucil® brand psyllium products from 1934 until 1985, at which time the brand was acquired by Procter and Gamble, which still markets several psyllium products under the Metamucil® brand. While initially and primarily marketed as a powder mixed with water, Metamucil® products and other psyllium products in the market have expanded to include tablets, capsules, and, more recently, fiber thin "cookies," including chocolate-flavored fiber thins, sometimes referred to as wafers, for both adults and children.

Metamucil powder and many other psyllium products have for several years been flavored. Such flavoring reflects the fact that psyllium is unappetizing in flavor, thus reducing consistent use, adoption, and compliance associated with the use of such products with treatment plans, recommended dietary regimens, and the like.

Furthermore, psyllium products known to date continue to be associated with other organoleptic/mouthfeel sensation problems which reduce adoption and consistent use of such products, or compliance in using such products as part of a recommended or prescribed health plan. Leading psyllium products are known by consumers to be associated with slimy gelling, which can make swallowing such products unpleasant if not difficult. See, e.g., Thomas Easley et al., The Modern Herbal Dispensatory, 2016, p. 52, https://books.google.com/books/about/The_Modern_Herbal_Dispensatory.html ?id=NY2xCwAAQBAJ ("Psyllium rapidly absorbs water, turning into a slimy gelatinous mass that is not very appealing."); Steve Taylor, Ed. Advances in Food and Nutrition Research, Vol. 55, 2008, p. 195, https://www.google.com/books/edition/Advances_in_ Food_and_ Nutrition_Rese arch/KN7ZBkLzwRoC?hl=en&gbpv=1& dq=advances+in+food+and+nutrition+research+acadennic+ press+2008&printsec=frontcover (describing psyllium products as being associated with an "unpleasant slimy mouth feeling"); and The Encyclopedia of Food Chemistry; Vol. 1; Peter Veralis, Laurence Melton, and Fereidoon Shahidi Eds., Elsevier; 2018; p. 67; available at https://books.google.com/books?id=MTV8DwAAQBAJ&source= gbs_navlinks_s (reporting an "unpleasant slimy nnouthfeel and undesirable flavor characteristics" associated with psyllium products).

The problem of psyllium taste and texture has led others to develop alternative forms of bulking/dietary fibers, such as inulin (a popular alternative fiber and prebiotic found in many types of plants), dextrin, and methylcellulose. Another alternative approach has been to propose mixtures of such alternative fibers with psyllium to reduce the negative properties of psyllium.

Psyllium wafers offer yet another means of psyllium supplementation. Psyllium wafers provide an added benefit of yielding a hunger satiation effect, as the consumption of a wafer offers a snack-like experience and provides calories from ingredients not found in pills, capsules, tablets, or powder forms. While wafers may provide a more positive consumption experience as compared to a powdered formulation or a pill/capsule/tablet, exposure to water during mastication and swallowing causes swelling and gelling in the mouth/throat. Further, the wafers often require the ingestion of multiple wafers per day, causing individuals to repeatedly endure the uncomfortable slimy feeling in their mouth and throat.

Another proposed approach to overcoming the organoleptic challenges associated with psyllium has been to combine the product with highly desirable foods, such as chocolate or sugar. Examples of proposed psyllium nutritional products described in patent disclosures that seek to address one or more of the shortcomings of psyllium products in such a way include those in U.S. Pat. No. 4,766,004 to Moskowitz and 4,568,557 to Becker (each and collectively describing a broad range of psyllium-rich coated and flavored compositions); U.S. Patent Publication Nos. 2002016844 (Mody), 20050238694 (Gerhardt), and 20050186306A1 (Sonneveld) (mostly describing similar coated psyllium products); and U.S. Patent Publication 20050271600 to Coleman (describing high concentration psyllium gummy chews containing an amount of a confectionary base). Despite the existence of such several attempts to propose such products in the patent literature, there are no associated chocolate-flavored psyllium products in the market that have addressed the issues reported above in association with psyllium products.

U.S. Patent Application 2011/0287134 (Ervin '134) similarly describes homogeneous blends of a high concentration of fiber (at least 20%, such as 20-59%, and preferably at least 40%), preferably composed of a blend of psyllium and inulin, with a high amount of chocolate (between 40% and 79%, with examples of actual embodiments of the alleged invention containing about 75% chocolate), along with a substantial amount of oil and added sugar. The Ervin '134 application discloses application and related know-how and was originally assigned to Antioxidant Superfoods, Inc. ("AOS"), of Naples, Fla., USA, but was subsequently assigned to the applicant, Lang Pharma Nutrition of Middletown, R.I., USA ("Lang").

After acquiring the Ervin '134 application, Lang sought to promptly commercialize products according to the Ervin '134 application. However, after attempting to scale up production of compositions according to the Ervin '134 application, Lang determined that such did not actually overcome the shortcomings of the prior art and failed to allow for economical mass production of a product suitable for the dietary supplement/nutrition market.

These facts demonstrate that despite the numerous prior proposals for developing chocolate-associated psyllium products in the art, the development of a psyllium-rich, chocolate flavored composition that is suitable for regular use by significant numbers of consumers requires a level of ingenuity that goes beyond any mere attempt to optimize these ingredients.

Principles of Construction

The following principles govern interpretation of this disclosure unless explicitly contradicted or clearly contradicted by context or plausibility.

All headings (e.g., "Principles of Construction") are used for convenience only and should not be construed as limiting the invention.

The terms "a," "an," and "the" and similar referents cover both singular and the plural forms of the referred element unless otherwise indicated herein or clearly contradicted by context (e.g., "a lipid" means "one or more lipids" and "the lipid" means "the one or more lipids"). Similarly, the use of an element or component in the singular is to be understood as also providing simultaneous disclosure and support for a plurality of the element or component. For example, discussion of a psyllium compound in one context should be understood as providing support for one, two, or more psyllium compounds unless clearly contradicted by context or an express contradictory statement. The converse also will be understood by those of ordinary skill in the art in reading this disclosure. In other words, the singular is intended to convey the plural and vice versa herein.

The recitation of ranges of values in this document is intended to serve as a shorthand method of referring individually to each separate value falling within the range within an order of magnitude of the order of the recited range, including the endpoints. For example, a recited range of 1-2 should be interpreted as providing support for 1.0, 1.1, 1.2, 1.3, . . . 1.9, and 2.0 and a recited range of 10-20 is to be interpreted as providing support for 10, 11, 12, 13, . . . 19, and 20). Unless otherwise indicated, each such separate value is incorporated into the specification as if it were explicitly individually recited herein. All ranges provided herein include the endpoints of the provided range, unless the exclusion of such endpoints is clearly stated or clearly indicated, regardless of the terminology used to describe the range. Unless otherwise stated, all exact values provided herein are representative of corresponding approximate values and vice versa (e.g., all exact exemplary values provided concerning a particular factor or measurement can also be considered to provide a corresponding approximate measurement, modified by "about," where appropriate; e.g., disclosure of "about 10" is to be understood as also providing support for 10 exactly as well as values of about 10).

Terms of approximation, such as "about" and "approximately" are used herein where measurements are understood to vary due to measurement limitation(s) or variability in populations, such as results of technical/scientific studies. The scope of such terms will depend on the context of the element at issue and the understanding of those skilled in the art. In the absence of such guidance in the art, through relevant teachings or examples, the term "about" should be understood as meaning +/−10% of the indicated value(s).

The term "also" means "also or alternatively."

Use of the term "or" herein is not meant to imply that alternatives are mutually exclusive unless clearly stated or clearly contradicted by context. Thus, in this disclosure, the use of "or" means "and/or" unless expressly stated or understood by one skilled in the art. In the context of any listed aspects of the invention written as depending on two or more other listed aspects, the use of "or" will be understood as referring to any of the referenced aspects. A "/" symbol between terms can signify an "or" or alternative names for an element or step, as will be clear from the disclosure/art.

All methods described herein can be performed in any suitable order unless otherwise indicated herein or otherwise clearly contradicted by context or plausibility. Unless clearly indicated or contradicted by context or plausibility, the elements of a composition disclosed herein (e.g., a pharmaceutical formulation) can be formulated in any suitable manner and by any suitable method. Unless otherwise explicitly stated or clearly contradicted by context, any combination of the various elements, steps, components, or features of the aspects of the invention described herein, and all possible variations thereof, is to be considered encompassed by the invention.

Numerous examples and aspects are provided in this disclosure to better illuminate the invention. No example, aspect, or combination or pattern thereof is intended to pose a limitation on the scope of the invention unless otherwise indicated. No language in the specification should be construed as indicating any element is essential to the practice of the invention unless as much is explicitly stated. Any of the exemplary embodiments should not limit the breadth and scope of the invention.

No claim or aspect of this document is intended to be interpreted as limited to "means-plus-function" construction unless such intent is clearly indicated by use of the terms "means for" or "step for." In particular, the use of the terms "configured to" or "adapted to" are not intended to suggest a "means-plus-function" interpretation, but, rather, suggest that the relevant component, composition, device, or element has been configured to, designed to, selected to, or adapted to achieve a particular referenced performance, characteristic, property, or the like.

Terms such as "including," "having," "containing," and "comprising" herein mean "including, without limitation." The description herein of any aspect or embodiment of the invention using terms such as "comprising," "having," "including," or "containing" an element simultaneously implicitly provides support for corresponding aspects wherein the aspect or embodiment "consists of," "consists essentially of," "sizably comprises," "predominantly comprises," and "essentially consists of," that particular element, unless otherwise stated or clearly contradicted by context.

The term "appreciable" and "appreciably" when used in relation to an amount of an ingredient/element in relation to a second, larger amount or whole (e.g., as in an amount of a composition or ingredient comprising "a sizable amount of" element A), means making up at least about 2% of the second, larger amount or whole (e.g., at least 5%, 7.5%, or 10%).

The terms "sizable" and "sizably" when used in relation to an amount of an ingredient/element in relation to a second, larger amount or whole (e.g., as in an amount of a composition or ingredient comprising "a sizable amount of" element A), means making up at least about 15% of the second, larger amount or whole (e.g., at least 20%, 25%, or 33%).

The terms "predominate" and "predominately" describe elements/ingredients that make up at least 50% of a larger amount or whole.

Similarly, use of terms such as "substantially", "in substantial amount", "materially," "in material amount," and the like with respect to an amount in relation to a larger amount/whole means that the amount makes up at least about 65% of the larger amount/whole (e.g., at least about 70%, at least about 75%, at least about 80%, or at least about 85% of the second amount or whole).

The phrases "consists essentially of" or "consisting essentially of" means that any step/element that maintains the fundamental features of the referenced element/step or retains the desired function of such element/step. The fundamental features & functions of elements and steps will be clear from the disclosure or the art. For ingredients, where features & functions are not clear, any such phrase should be interpreted as meaning "essentially all," as described in the following paragraph.

Terms such as "essentially all," "essentially entirely," or "essentially comprise" when used in connection with a referenced amount and a larger amount/whole mean that the smaller referenced amount makes up at least about 90% of a larger amount/whole (e.g., at least about 91%, 92%, 93%, 95%, 96%, 97%, 98%, or at least about 99% of the larger amount or whole).

Changes to tense or presentation of phrases defined herein (e.g., using "comprises predominately" instead of "predominately comprises") do not modify the meaning of the defined phrase.

The terms "significantly" or "significant" refer to results that are statistically significant using an appropriate statistical test (e.g., $p \leq 0.05/0.01$).

Any reference to "combination" or "combinations" of listed elements means combination(s) of any or all thereof.

All references, including publications, patent applications, and patents, cited herein, including the patents and patent applications cited above, are hereby incorporated by reference to the same extent as if each reference were individually and specifically indicated to be incorporated by reference and were set forth in its entirety herein. Accordingly, the reader should review and consider such references in understanding the full content of this disclosure. For example, unless clearly contradicted by context or explicit statement, the disclosure of such documents relating to formulations, methods of production, and methods of use of compositions and devices can be combined with the teachings provided herein to provide additional useful compositions and applications. However, the citation and incorporation of patent documents herein is limited to the technical disclosure of such patent documents and does not reflect any view of the validity, patentability, or enforceability of any such patent applications or patents or the validity of such references as prior art.

The term "here" means "in this disclosure." The abbreviation "OTI" means "of the invention." The abbreviation "ITA" means "in the art."

No part of this disclosure should be construed as indicating any element/step is essential to the practice of the invention.

Unless clearly indicated, the scope of any aspect or embodiment of the invention is not limited to any exemplary processes, compositions, or methodologies described here. The terminology used in the description is to describe versions or embodiments only and is not intended to limit the scope of the invention. Unless defined otherwise, all technical and scientific terms used herein have the same meanings as commonly understood by one of ordinary skill in the art. Any methods and materials similar or equivalent to those described herein can be used in the practice or testing of embodiments of the invention, the methods, devices, and materials described herein.

Scope and Meaning of Terms Specific to this Disclosure

Because certain terms specific to this disclosure may be used differently in the art, provided here is guidance concerning the scope and meaning of a selection of such terms.

Use of the abbreviation "NC" means "nutritional composition" and can refer to any one or more compositions of the invention.

The term "component" in this disclosure (e.g., a lipid component) typically refers an ingredient or collection of ingredients incorporated into a nutritional composition, which is defined by one or more characteristics. Each "component" described here can contain several different ingredients and such ingredients can comprise a mixture of other ingredients (e.g., a lipid component can contain cocoa butter and coconut oil and a chocolate component can contain a dark chocolate ingredient or a milk chocolate ingredient, each of which can contain other components such as milk fats, cocoa butter, sugar, emulsifier(s), and cocoa/cacao). When a composition is in its finished/ready state (i.e., ready for consumption), most, at least materially all, or at least essentially all, of the components are blended or otherwise mixed, as described below. However, because the amount and characteristics of the components and ingredients provide functional properties to the composition, they are used to describe the compositions of the invention, as are the overall (total) characteristics of the compositions.

Terms such as "fat" and "lipid" may, in some fields of art, be used synonymously. Here, the term "lipid" here is used to describe substances that are insoluble in water and soluble in nonpolar solvents, such as alcohol, ether, and chloroform, are safe for human consumption, and can be nutritious. Typically, lipids are predominately, essentially, or entirely composed of hydrocarbons and in aspects are predominately, essentially, or entirely composed of fatty acids.

A lipid ingredient typically can be at least predominately, at least materially, at least essentially, or is entirely composed of lipids (e.g., is at least 65%, at least 75%, at least 85%, at least 95%, at least 97%, or at least 99% or 100% composed of lipids). Many lipid ingredients, such as coconut oil, typically entirely consist of lipids due to separation/purification of lipids from other source materials.

The terms "fats" and "oils" are used here to describe classes of lipids. A "fat" in this disclosure means a lipid that is predominately, essentially, or entirely solid at room temperature and normal atmospheric conditions. The term "oil" here is used to refer to any edible lipid that is predominately, essentially, or entirely liquid under such conditions.

Typically, fats sizably comprise, predominately comprise, materially comprise, essentially comprise, or consist of saturated fatty acids, particularly triglycerides. Typically, oils sizably comprise, predominately comprise, materially comprise, essentially comprise, or consist of unsaturated fatty acids. Given their difference in composition and chemistry, saturated fatty acids and unsaturated fatty acids exhibit significantly different nutritional and compositional properties.

Fat ingredients can be ingredients which are typically solid at room temperature ("RT") but which can in aspects be comprised of both saturated lipids (or fats, typically solid at RT) and unsaturated lipids (or oils, typically liquid at RT). Cocoa butter and coconut oil are examples of such fat ingredients. Any description of the state of an ingredient or component at RT implicitly also means at normal/typical atmospheric conditions (about 1 atm/about 14.7 psi). An "oil" also may contain some amount of fat, but an oil will at least predominately, materially, or essentially be composed of lipids, usually unsaturated lipids, that are liquid at RT.

In some aspects, the terms "lipid," "oil," and "fats" can also be used to refer to nutritional ingredients, that are at least predominately, materially, or essentially composed of lipid, oil, or fat, respectively, but may contain other components. Thus, e.g., cocoa butter herein is classified as a fat because it is a composition that is at least predominately lipid in composition and is solid at room temperature and normal pressure.

The term "dietary fiber" means any fiber that the US Food and Drug Administration or corresponding international regulatory body has recognized as dietary fiber as of the date of this disclosure. References to fiber herein implicitly mean fiber that would be recognized as dietary fiber by such regulatory authorities.

The terms "user" and "consumer" both refer to a person that consume nutritional products of the invention.

SUMMARY OF THE INVENTION

This disclose describes new and inventive soluble fiber and lipid rich flavored nutritional compositions that are useful in, among other things, the management of appetite, regularity, glucose control, and other dietary fiber-related health matters including, e.g., reducing risk of heart health/disease, stroke, obesity, or type 2 diabetes, and related ailments.

Nutritional compositions of the invention ("nutritional compositions" or "NCs") comprise (a) a fiber component comprising one or more soluble dietary fiber ingredients comprising psyllium or a soluble dietary fiber that has similar water absorption characteristics as psyllium (e.g., in terms of swelling and gelling and negative organoleptic properties), (b) a lipid component comprising one or more fats, and (c) a flavoring component (e.g., a chocolate component defining the primary flavor of the composition, commonly defining a base for the composition). The amounts and characteristics/composition of these components, alone or in combination with other components/ingredients, provide measurably or significantly improved characteristics over similar currently on-market and previously proposed psyllium compositions, including with respect to measurably or significantly improving organoleptic properties, consumer adoption and/or sustained use, or ease of commercial production.

The soluble fiber component ("fiber component") of NCs is at least predominately, at least materially, or at least essentially composed of one or more sources of soluble dietary fiber. In aspects, the fiber component is at least predominantly composed of, at least materially composed of, or at least essentially composed of (e.g., is at least about 95% composed of), or is entirely composed of psyllium. In aspects, NCs comprise about 8.5 wt. % to about 18.5 wt. % psyllium, such as about 10-18.5 wt. % psyllium, e.g., about 11-18 wt. % psyllium, e.g., about 12-17 wt. %, about 13-17 wt. %, or 13-16 wt. % psyllium fiber). In aspects, compositions of the invention can be characterized by lacking significant amounts (e.g., 5% or more, 2% or more, 1% or more, 0.5% or more, or 0.1% or more) of soluble/dietary fiber sources other than psyllium, such as inulin. In aspects, compositions described herein lack any detectable amounts of soluble/dietary fiber sources other than psyllium, such as inulin. In aspects, some, most, materially most, e.g., at least about 50%, at least about 60%, at least about 80%, at least about 90%, at least about 95%, or at least about 99% of psyllium in the composition has a mesh size of at least 33. In aspects, the average mesh size of psyllium in the composition also or alternatively is between about 40-60.

The lipid content of NCs is typically at least sizably or at least predominately composed of saturated lipids. In aspects, compositions comprise about 15-25 wt. % total saturated lipid, such as about 16-21 wt. % saturated lipid (e.g., about 16-19 wt. % saturated lipid). In some respects, the amount of saturated lipid content of NC's is less than 20 wt. %.

In aspects, the amount of oil used in making the compositions, such as for example canola oil, is less than about 2.5 wt. %, such as less than about 2.4 wt. %, less than about 2.3 wt. %, less than about 2.2 wt. %, or less than about 2.1 wt. %, such as less than about 2.05 wt. %.

In aspects, the ingredients of the NC comprise between 10-18 wt. % (e.g., 11 wt. %-15 wt. %, or 12-14 wt. %) unsaturated lipids. Thus, e.g., the invention provides nutritional compositions comprising 10-18.5 wt. % psyllium fiber, 10 wt. %-18 wt. % unsaturated oil, 16-21 wt. % saturated lipid, the saturated lipid to unsaturated lipid/oil ratio optionally being more than 1.

In aspects, NCs comprise a texturizing element that further enhances the organoleptic or nutritional properties of the NC. In aspects, the texturizing element can comprise a non-soluble fiber. In aspects, NCs comprise at least 5 wt. %, at least 6 wt. %, or at least 7 wt. % of a texturizing element (e.g., about 5-15 wt. % of a texturing element, or about 5-15 wt. % of a texturizing element), such as a rice crisp, protein crisp, a combination thereof, or similar texturizing element. In certain embodiments, the texturizing element will sizably, predominately, materially, essentially entirely, or entirely be composed of a material having a density of at least about 0.1 g/cm$^3$ (g/cc). As with all aspects described herein, this aspect can be combined with any other aspect of this disclosure. For example, the invention provides compositions comprising 10-18.5 wt. % psyllium, 50-75 wt. % chocolate, 10-18 wt. % (e.g., 10 wt. %-15 wt. %) unsaturated lipid, 16 wt. %-25 wt. % saturated lipid (e.g., 16 wt. %-21 wt. % saturated lipid, or 16-19 wt. % saturated lipid), and at least about 5 wt. % of a texturizing element (e.g., at least about 7 wt. % of a texturizing element), which texturizing element has a density of at least about 0.1 g/cm$^3$ and commonly has a density of at least about 0.2 g per cubic cm.

In aspects, NCs are not formed from extrusion (i.e., are non-extruded compositions). In aspects, NCs also are not coated (e.g., the compositions lack any chocolate coating or coating of any coating layer). In aspects, the chocolate component is the predominate, materially only, essentially only, or only flavoring (e.g., the NC lacks any other flavoring component). In aspects, less than about 5 wt. %, less than about 2.5 wt. %, less than about 1 wt. %, less than about 0.5 wt. %, or less than about 0.25 wt. % of the composition is made up of flavoring agents (flavorants) that are separate from the chocolate component. An NC also typically lacks any chocolate flavoring; such as any chocolate flavoring, not meeting a regulatory authority definition of "chocolate", e.g., as defined by US FDA. NCs also are typically substantially homogeneous in composition. NCs also typically comprise no detectable amount of water, e.g., less than 1 wt. % water. Any one or more of these characteristics of the nutritional compositions of the invention can be applied to any of the aspects described elsewhere herein.

According to embodiments, NCs contain a limited amount of one or more emulsifiers, such as lecithin (outside of the chocolate component, in total, or both). In aspects, other than in any chocolate ingredients, NCs comprise about 0.25 wt. % or less of an emulsifier (e.g., a lecithin). In aspects, NCs comprise between about 0.05 wt. % and 0.2 wt. % lecithin outside of any chocolate component, such as 0.05 wt. %-0.175 wt. % or 0.05 wt. % and 0.125 wt. % of a lecithin (e.g., soy or sunflower lecithin). Again exemplifying how all aspects of this disclosure can be combined, the invention provides NCs comprising 10-18.5 wt. % psyllium, 50-75 wt. % of a chocolate component, at least about 28 wt. % total lipid (e.g., 16-21 wt. % saturated lipid or 10-15 wt. % unsaturated lipid) at least a sizable amount of which is contained in the chocolate component and the rest in a lipid component; at least 5% of a texturizing element (e.g., at least about 7 wt. % of a texturizing element), wherein (a) optionally no more than about 2.1 wt. % of the composition is attributable to any oil ingredient(s), (b) optionally at least about 5 wt. % (e.g., at least 6 or 7 wt. %) of the NC is attributable to a solid lipid (a fat), and (c) the NCs contains about 0.05 wt. %-about 0.2 wt. % lecithin, such as 0.05 wt. %-0.175 wt. % lecithin in the composition, outside of the chocolate component.

The nutritional products of the invention can exhibit measurably or significantly improved organoleptic properties (e.g., the flavor, texture, or mouthfeel, as experienced by the typical consumer) (e.g., with respect to currently available psyllium products, such as Metamucil® wafer products or products described in the above-referenced prior art), which can lead to better rates of adoption and sustained use, while maintaining the benefits of a high psyllium fiber diet such as reduced constipation, caloric management, etc.

The invention also provides methods comprising administering nutritional compositions of the invention, such as any of the above-described compositions, to individuals/consumers (e.g., to dieters). In one aspect, the invention provides a method of supplementing a diet comprising administering to an individual about between 5 g, about 7.5 g, or about 10 g (e.g., 12 g, 15 g, 20 g, 24 g, or 25 g) and about 50 g, about 70 g, about 80 g, about 90 g, or about 100 g of the nutritional composition (e.g., about 5-150 g, about 7.5 g-125 g, about 10 g-100 g, or about 12-96 g of such a composition), e.g., per intake or per day. According to embodiments, such a method also or alternatively can be characterized in providing between about 2 g, about 2.5 g, or about 3 g, such as at least between about 3.1 g or at least about 3.2 g and about 10 g, about 12 g, about 12.5 g, about 13 g, about 14 g, about 15 g, about 20 g psyllium, or about 25 g of psyllium to the individual, e.g., per intake or per day. Thus, for example, the invention provides methods that comprise administering between about 10 g-about 100 g of a nutritional composition comprising about 8.5-18.5 wt. % psyllium, about 50-75 wt. % chocolate, at least about 28 wt. % lipid (e.g., about 28-38 wt. % lipid, which optionally is predominately saturated lipid, which optionally comprises 16-21 wt. % saturated lipid or 10-15 wt. % unsaturated lipid), optionally about 5-15% of a texturizing element (optionally that has a density of at least about 0.1 g/cubic cm and commonly a density of at least about 0.2 g/cm$^3$), to the individual, for one or more days. Such amounts of the composition can be provided to the individual in units ("administrations" or "servings") of about 5 g-50 g, such as about 7.5 g-about 35 g, e.g., about 10 g-about 30 g (e.g., 12-24 g). Servings can correspond with meals, snacks, or a combination thereof. In some aspects, supplementation with the compositions described herein comprises a method of escalating amounts (e.g., in escalating "doses") from a first time period (e.g., about 2-14 days, e.g., 3-10 days, 4-8 days, or about a week) to at least a second period (which can be indefinite), such as for example to allow the body of the consumer to become accustomed to a composition before increasing the amount of composition(s).

For example, in one embodiment the invention provides a method of dietary regulation that comprises (a) 1-3 servings of a nutritional composition with a mass of about 20-35 g, e.g., about 25 g (such as 24 g), taken in association with a meal, such as before a meal, for a total of, e.g., about 20 g-about 100 g and (b) 1-6 snack servings, such as 2-4 snacks, of servings of about 25-75%, such as 33-66%, such as about 50% of the meal serving, e.g., about 2.5 g-15 g, such as about 5 g-14 g, such as about 7.5 g-12.5 g, e.g., about 10 g, 11 g, or 12 g. Packages of the nutritional composition can be provided in a manner that facilitates such administration, e.g., by scoring ½, ⅓$^{rd}$, or ¼th servings, and by being provided in recommended serving sizes, e.g., of about 20 g-about 30 g, such as about 24 g, each serving providing at least 3 g, and preferably at least 3.15 g, such as at least 3.2 g of psyllium fiber. In aspects, a recommended serving size can comprise multiple, individually wrapped final products, such as for example each individually wrapped final product representative of about ½ a serving size. For example, a serving size can be approximately 24 g of a nutritional composition, provided to the consumer as 2 individually wrapped about 12 g products, each individually wrapped product providing about ½ of the total amount of psyllium fiber per serving, for a total amount of psyllium per serving of at least about 3 g, for example about 3.2 g or about 3.3 g, or about 3.4 g, or about 3.5 g or about 3.6 g.

Some NCs can be characterized by requiring less water for comfortable consumption or to ensure the safety of the individual as compared to currently marketed psyllium products. For example, in one embodiment, the invention provides methods, such as those described above, wherein a method comprising consumption of an NC product comprises the individual co-consuming less than 8 oz of water per every at least 3 g, at least 3.1 g, at least 3.2 g, at least 4 g, or at least 5 g of psyllium, on a serving, snack, or daily basis. In one embodiment, a method is provided that comprises an initial minimum amount of water to be co-consumed with the psyllium-containing composition, which is reduced over a period of recommended consumption (as part of a diet plan of at least about 5 days, at least about 1 week, at least about 10 days, at least about 2 weeks, at least about 3 weeks, at least about 1 month, or longer).

Methods of the invention can, in aspects, be used to promote health in any of the various ways that psyllium products are known to be useful, such as those described in the Background of this disclosure and elsewhere herein (e.g., in regulating excessive caloric intake, constipation/assuring regularity in bowel movements, in managing high cholesterol, or in assisting with a combination of any or all thereof).

According to one embodiment, the individual using nutritional compositions/products of the invention in a method of the invention is an individual that has previously received a recommendation for, or attempted adoption of, a fiber-rich or more specifically a psyllium-rich diet or health plan, but has failed to maintain the regimen consistently, wherein the individual's adoption of the product is greater, the individual's compliance with using the product is greater, or both. Thus, for example, in an aspect, the invention provides a method of supplementing fiber in the diet comprising administering about 10 g-100 g, such as about 50 g-100 g, e.g., about 70 g-90 g of a nutritional product comprising about 10-18.5 wt. % psyllium, about 50-75 wt. % chocolate, and about 25-40 wt. %, such as about 25-37.5 wt. %, or such as about 28-35 wt. % total lipid (which optionally is sizably or predominately saturated lipid, such as in comprising about 16-21 wt. % saturated lipid), optionally comprising about 5-15 wt. % texturizing material, and optionally comprising less than about 0.2 wt. %, such as less than about 0.1 wt. % of lecithin attributable to any ingredient other than the chocolate, in serving/snack sizes of 2-6 times, e.g., 3-5 times or 3-4 times per day, over a period of one week or longer, two weeks or longer, wherein optionally the method is associated with consumption of a lower minimum amount of water than currently recommended for Metamucil® products, optionally where the individual has improved compliance in using the product on a recommended basis than in previous experience with psyllium products or where the product is recommended to a person that has previously failed to have a positive experience with psyllium products.

Such embodiments and additional aspects and features of the invention will be described further in the following Detailed Description of the Invention. To aid the reader, parts of the Detailed Description will focus on particular elements of the inventive compositions or methods. However, unless otherwise indicated any aspect, feature, embodiment, component (ingredient), step, or method of the invention can be combined with any other such aspect, feature, embodiment, component (ingredient), step, or method, and the focus on the particulars of any aspect should not be interpreted as a limitation of any aspect, but, rather, as providing possible details for any such element, feature, step, etc., that can be combined with the various descriptions of inventive compositions and methods provided herein, unless otherwise explicitly stated or clearly contradicted by context.

DETAILED DESCRIPTION OF THE INVENTION

The invention provides high-fiber, lipid-rich, and chocolate flavored nutritional compositions, which comprise a fiber component that is mostly composed of psyllium or a source of fiber having similar properties to psyllium (e.g., in terms of gel formation in water), but which possess texture and flavor characteristics that encourage adoption and routine consumption of the fiber-rich product while avoiding negative drawbacks associated with current on-market psyllium products, such as uncomfortable gelling or slimy mouthfeel.

Nutritional compositions described here can be associated with detectably or significantly improved adoption, sustained use, consistent use, and overall preference over other psyllium products. As such, nutritional compositions described herein can form part of a more reliable psyllium-based dietary plan than such other products. The products described here also or alternatively are associated with improved properties over previously proposed similar products in terms of feasible and economical manufacturing at scale, allowing such products to be offered at a reasonable price to the mass market.

In aspects, nutritional compositions can have viscosity, gel content/rheology, or water-absorption characteristics, such that such NCs can be successfully and economically manufactured using traditional food product manufacturing techniques and equipment, such products enjoyed without the negative drawbacks of traditional psyllium products in terms of a significant number of consumers experiencing unpleasant gelling or other organoleptic sensations in the mouth/throat, during mastication and swallowing, which reduce adoption, sustained use, or preference for the product as compared to previously described similar compositions or on-market psyllium products (e.g., Metamucil® wafer products). In aspects, nutritional compositions and related methods provided herein exhibit significantly similar or significantly improved effects with respect to currently on-market psyllium products in terms of dietary fiber supplementation, appetite management, regularity management, wellness management, and similar psyllium-related dietary matters.

In an exemplary aspect, a nutritional composition contains at least 10% by weight of psyllium and no more than 18.5% by weight of psyllium; at least 50% by weight of chocolate, and no more than 75% by weight of chocolate; at least 16% by weight saturated lipid and no more than 21% by weight of saturated lipid; at least 10% by weight unsaturated lipid and no more than 18% by weight of unsaturated lipid; and at least 5% by weight (e.g., at least 7% by weight) of a texturing element. In aspects, the texturing element can have a density of at least 0.1 g/cm$^3$, commonly at least 0.2-g/cm³ (g/cc), such that the texturizing element will be characterizable as being substantially homogeneously distributed throughout the composition (such as, for example, no 25% of a final product (e.g., a bar) differs from any other 25% of a final product in content of a texturizing element by more than 50%). Homogeneity-related aspects of the NC are discussed in more detail elsewhere herein.

In another exemplary aspect, the invention provides methods for suppressing appetite, promoting digestive regularity, easing constipation, or otherwise regulating health by supplementing the diet with between about 10 g and about 100 g of a nutritional composition containing at least 10% by weight of psyllium, and no more than 18.5% by weight of psyllium; at least 50% by weight of chocolate, and no more than 75% by weight of chocolate; at least 16% by weight saturated lipid and no more than 21% by weight of saturated lipid; at least 10% by weight unsaturated lipid and no more than 18% by weight of unsaturated lipid; and at least 5% (e.g., at least 7%) by weight of a texturing element wherein the texturing element can have a density of at least 0.1 g/cm³ (g/cc), commonly at least 0.2-g/cm³ (g/cc), such that the texturizing element will be substantially homogeneously distributed throughout the composition as described elsewhere herein.

To help illuminate the aspects of the invention the following sections of this description primarily focuses on particular components/ingredients and characteristics. However, any facet of any such described aspect can be combined with any facet of any other aspect.

Fiber Component/Ingredient(s)

The nutritional compositions of the invention comprise a fiber component at least predominately made up by one or more soluble dietary fiber-containing materials, which generally at least sizably comprise, at least predominately comprise, or at least essentially comprise psyllium or a source of soluble fiber having art-recognized or physiochemically demonstrated similar characteristics as psyllium in terms of water absorption, gelling, and the like.

In one aspect, the amount of soluble dietary fiber in the composition (e.g., the wt. % of psyllium) can be any amount effective for maintaining bowel regularity, providing a feeling of satiety, or both maintaining bowel regularity and for providing a feeling of satiety (e.g., in a significant amount of a population as determined through adequate scientific study (ies)).

In aspects, the one or more fiber ingredients (fibers) in in the composition can be any one or more fiber materials sufficient for desired weight maintenance and to promote healthy bowel function.

In aspects, the fiber component of the composition comprises a soluble fiber component or ingredient, comprising one or more non-psyllium soluble fiber materials, such as fiber material obtained from oats, barley, flaxseed, bran flakes, fruits, or vegetables as an alternative to or in addition to one or more psyllium materials.

In aspects, the soluble fiber component of the composition comprises, sizably comprises, predominately comprises, materially comprises, essentially comprises, or consists of psyllium. In aspects, at least about 75%, at least about 80%, at least about 85%, at least about 95%, at least about 97%, or at least about 99% of the soluble fiber in the composition is psyllium. In certain aspects, the psyllium contributes at least about 90% of the soluble dietary fiber of the composition, such as for example at least about 92%, at least about 94%, at least about 96%, at least about 98%, at least about 99%, or even at least about 99.5% of the soluble dietary fiber of the composition is attributable to psyllium.

In aspects, at least about 5 wt. %, at least about 7.5 wt. %, or at least about 8.5 wt. % of a nutritional composition is composed of a fiber component. According to certain embodiments, the nutritional composition of the invention provides between about 8-25% of the daily value (DV) of dietary fiber per serving (e.g., as set by US FDA standards), sometimes referred to herein as the percent daily value, % DV, or PDV. In one embodiment, the composition can preferably provide between about 11-24% of the dietary fiber DV, or between about 12-23%, or between about 13-22%, such as between about 13-20 wt. %, or between about 16-20 wt. %, or between about 17-19 wt. % of the daily value of dietary fiber per serving. In aspects, an NC can comprise between about 8.5-18.5 wt. %, such as between about 10-18.5% psyllium, which provides between about 16-20% of the daily value of dietary fiber per serving.

In aspects, when less than a full serving size is consumed, the percent daily value of dietary fiber is adjusted accordingly. For example, in aspects, a single unit of composition can represent a fraction of a serving size (e.g., 1/2 serving). In such aspects, a single unit can provide approximately 2-approximately 11.5%, such as about 3-10.5%, about 4-9.5%, or for example about 5-8.5% daily value of dietary fiber. In certain aspects, total consumption per day can comprise a fraction of a full serving or multiple servings, providing, for example, between about 5-50% daily value of dietary fiber, such as for example between about 6-49% or e.g., between about 6-48% DV, or for example between about 7-47% DV, 7-46% DV, 7-45% DV, 7-44% DV, 7-43% DV or for example between about 7-42% DV of dietary fiber.

A psyllium ingredient in the fiber component can comprise both soluble and insoluble fiber material. In some aspects, at least about 50%, at least about 55%, at least about 65%, at least about 70%, at least about 75%, at least about 80%, at least about 85%, at least about 90%, or at least about 95% of the psyllium in such a composition is classifiable as soluble fiber (such compositions may sizably contain, predominately contain, contain in clear majority, essentially only contain, or only contain psyllium husk as opposed to psyllium seed material). In aspects, the psyllium can comprise between about 50-80% soluble fiber, such as for example between about 55-75% soluble fiber, or e.g., between about 60-70% soluble fiber.

In some aspects, the nutritional composition of the invention comprises between about 5-20 wt. % soluble fiber, such as between about 5 and about 19 wt. %, such as between about 5.5-18.5 wt. %, between about 6.5-18.5 wt. %, between about 7.5-18.5 wt. %, or about between about 8-18.5 wt. %. In more particular aspects, the compositions of the invention comprise about 5.5-17.5 wt. %, such as between about 6-17 wt. %, between about 6.5-17 wt. %, between about 7-17 wt. %, between about 8-17 wt. %, or between about 7-13 wt. % of soluble fiber.

In aspects, most (at least 50%) or at least materially most, e.g., at least about 60%, at least about 70%, at least about 80%, at least about 85%, at least about 90%, at least about 95%, at least about 99%, at least 99.5%, or at least 99.9% of psyllium in the composition has a mesh size of at least 33, e.g., at least 35. In aspects, the average mesh size of psyllium in the composition also or alternatively is between about 40-60. In aspects, predominately all, materially all or at least essentially all the psyllium in the composition also or alternatively has a mesh size of about 40-60. In aspects, the average mesh size of the psyllium in the composition is at least 35.

In aspects, the composition comprises psyllium both from a mesh powder ingredient and psyllium whole husk ingredient. In one aspect, the amount of psyllium present as a mesh powder is greater than that of psyllium present as a whole husk (e.g., the ratio of psyllium present having a mesh size of at least 33 to the psyllium present as a whole husk is greater than 1). In aspects, the ratio of mesh powder psyllium to whole husk psyllium is, e.g., about 1.1:1, about 1.25:1, about 1.33:1, about 1.5:1, about 1.75:1, about 3:1, about 4:1, about 5:1, about 8:1, about 10:1, about 15:1, or about 20:1 or a range defined by any combination of such values. In some aspects, more psyllium is present as a whole husk than as a mesh powder in a composition, such as, e.g., greater than about 50%, such as about 52%, about 55%, about 57%, about 60%, about 62%, or about 65% or more of the psyllium in the product is present in whole husk form. In aspects, the ratio of whole husk psyllium to mesh powder psyllium is about 1.1:1, about 1.25:1, about 1.33:1, about 1.5:1, about 1.75:1, about 2:1, about 3:1, about 4:1, about 5:1, about 8:1, about 10:1, about 15:1, or about 20:1 or a range defined by any combination of such values. In aspects, the mesh size of the mesh power psyllium is any of the mesh sizes or mesh size ranges described in the preceding paragraph. In aspects, less than about 10%, less than about 7%, less than about 5%, or less than about 3%, 2%, or 1% of the psyllium is whole husk psyllium. In aspects, a composition lacks any detectable or significant amount of whole husk psyllium.

In some aspects, psyllium contributes at least 90% of the total fiber in the composition, such as at least about 91 wt. %, at least about 92 wt. %, at least about 93 wt. %, at least about 94 wt. %, at least about 95 wt. %, at least about 96 wt. %, at least about 97 wt. %, at least about 98 wt. %, or at least about 99 wt. % of the total fiber in the composition. In some aspects, psyllium is the only dietary fiber ingredient in the nutritional composition contributing more than about 10% of the amount of dietary fiber in the composition to the composition, such as contributing more than about 11%, more than about 12%, more than about 13%, more than about 14%, more than about 15%, or more than about 16% of the total amount of dietary fiber in the composition to the composition. In aspects, the psyllium in the composition also provides at least about 80%, at least about 90%, at least about 90%, at least about 98%, or at least about 99% of the soluble fiber in the composition or total fiber in the composition. In aspects, the composition is free of detectable amounts of any other source of soluble fiber (e.g., in aspects NCs are free of inulin).

In embodiments, the nutritional composition comprises at least about 5 wt. % psyllium, such as at least about 7 wt. % psyllium, such as at least about 8.5 wt. % psyllium, e.g., at least about 10 wt. %, at least about 11 wt. %, at least about 12 wt. %, or at least about 13 wt. % psyllium. In aspects the composition comprises at least about 14 wt. % or 15 wt. % psyllium.

According to embodiments, the nutritional composition comprises less than about 20 wt. % psyllium, such as less than 18.5 wt. % psyllium. For example, the maximum amount of psyllium in the composition can be about 18 wt. %, about 17.5 wt. %, about 17 wt. %, about 16.5 wt. %, about 16 wt. %, about 15.5 wt. %, or about 15 wt. %. In aspects, NCs have a maximum psyllium content of about 19 wt. %, about 18.5 wt. %, or about 18 wt. %. In aspects, NCs have a maximum psyllium content of about 17 wt. %, such as a maximum of about 16 wt. %, or such as a maximum of 15 wt. % psyllium.

In aspects, the invention provides nutritional compositions comprising, e.g., about 7-19 wt. % or about 8-19 wt. %, such as about 8.5-18.5 wt. %, e.g., about 9-19 wt. % or about 9-18.5 wt. %, e.g., about 10-18.5 wt. % or about 10-18 wt. %, such as about 11-18 wt. % or about 11-17.5 wt. %, e.g., about 12-18 wt. %, about 12-17.5 wt. %, about 12-17 wt. % psyllium, about 13-17% psyllium, or about 13-16% psyllium, such as about 12.5-15.5 wt. %, about 12-15 wt. %, about 12-14 wt. %, about 13-16 wt. %, or about 12 wt. %, about 13 wt. %, about 14 wt. %, 14.5 wt. %, or about 15 wt. % psyllium. In aspects, nutritional compositions contain psyllium in an amount ranging between 10-20 wt. %, such as between about 10-20 wt. %, between about 10-18 wt. %, between about 10-15 wt. % psyllium.

According to aspects, a serving of the nutritional composition can be in, e.g., a form that is convenient for carrying or administration, such as a bar. The presentation of the nutritional composition as a bar may also aid in the adoption of the product, given the association of bars with nutritional bars, candy bars, and the like. Although a bar may be a typically preferred embodiment, the composition can be in other forms, such as, for example, but not limited to, cookies, wafers, or ball-shaped, wafer-shaped, letter-shaped, geometric-shaped (e.g., generally cubed or cylindrically shaped), or stick-shaped snacks (or suitable combinations of any or all thereof). Nutritional compositions of the invention will often be described in terms of bars for convenience. Accordingly, the terms "bar" and "serving" are to be understood as providing support for one another here, though bars as a presentation are, as indicated, a specific embodiment of the invention. Also, aspects described herein in relation to compositions can be applied to bars/servings and vice versa, by considering any described serving/bar amount of NC. In aspects, a single serving size can be divided into two or more separately packaged final products, such as bars. In aspects each individually packaged bar can equal a fraction of a serving size. In aspects, a serving size can consist of, e.g., 2 bars, each bar contributing about half of the total amount of each ingredient per serving. The terms "bar" and "serving" herein implicitly disclose and support corresponding embodiments where "bar" is plural, and multiple bars represent a single serving.

In some aspects, the amount of total dietary fiber provided per serving (e.g., per single serving size bar or per serving comprising multiple individual bars) is between about 1-10 g, such as about 2 g-about 8 g, e.g., about 1 g-about 7.5 g, about 2 g-about 6 g, about 2.5 g-about 7.5 g, about 2.5 g-about 5 g, about 2.5 g-about 6 g, about 2.5 g-about 5 g, or about 2.5 g or about 3 g-about 4 g. In one aspect, the composition can comprise between about 2-8 g dietary fiber, such as about 3-7 g, or such as between about 4-6 g of total dietary fiber per bar. According to embodiments, each serving of the composition comprises at least about 3.1 g, e.g., at least about 3.15 g, e.g., at least about 3.2 g of dietary fiber.

In aspects, a nutritional composition comprises approximately 1 g to about 8 g, such as about 1 g to about 6 g or about 1 g to about 5 g of soluble fiber per serving/bar, such as between about 1-5 g, between about 1-4 g, between about 1-3 g, between about 1-2 g, between about 2-4 g, between about 2-3 g, between about 3-5 g, between about 3-4 g, or for example between about 4-5 g of soluble fiber per serving. In aspects, a serving will contain more than 1.5 g of soluble fiber per serving, such as at least 1.6 g, at least 1.7 g, or at least 1.8 g of soluble fiber per serving (e.g., a serving can contain 1.5-2.6 g, 1.6-2.5 g, or 1.8-2.4 g soluble fiber per serving). In aspects, NCs comprise at least at least about 3 g, such as at least about 4 g or at least about 5 g of dietary fiber per serving, comprising about 3 g of psyllium, such as at least about 3.1 g, at least about 3.2 g, or at least about 3.4 g of psyllium per serving, the psyllium, in aspects, contributing between about 1 g to about 3 g of soluble fiber per serving, such as between about 1.5-about 3 g soluble fiber per serving.

In aspects, the amount of dietary fiber provided in a single serving of an NC represents between 12% and about 16% Daily Value (% DV) for fiber in the diet (e.g., per US FDA standards). In aspects a 2,000-calorie diet is used for setting the DV/general nutrition advice. In aspects, the % DV of fiber provided by a single serving of an NC is about 12%, about 13%, about 14%, about 15%, or about 16%.

In one aspect, a nutritional composition is provided that is in the form of a single-serving finished product. In one aspect the single-serving product comprises a serving size of about 15-35 g, about 17.5-35 g, about 20-35 g, about 22-32 g, about 22-30 g, about 23-28 g, or about 24-30 g, for example about 24 g, or about 25 g, or about 26 g, or about 27 g, or about 28 g, or about 29 g, or about 30 g.

In aspects, the invention provides a single-serving NC product. In aspects, methods of the invention include consuming one single-serving of the composition per day. In aspects, the single-serving product is a single-serving finished product wherein more than one sub-serving (e.g., one or more meal servings or snack servings) is consumed per day. In aspects, a single-serving product is provided 1, 2, 3, 4, or 5 times a day as part of a method of use.

In one embodiment, servings are provided as meal servings, which may comprise about 10 g-30 g of an NC of the invention, such as about 12.5 g-27.5 g, e.g., about 15-27.5 g, e.g., about 20-30 g, such as about 22-28 g, e.g., about 23-28 g or about 23-25 g, such as about 24 g of the NC.

In exemplary embodiments, a composition can be in the form of a 24 g finished serving-sized product containing between about 2-5 g of psyllium, such as between about 3-4 g of psyllium, or about 3-4.5 g of psyllium, such as between about 2-4 g of psyllium, or about 2.5-3.5 g of psyllium. In embodiments, a serving or partial serving (e.g., in aspects where a partial serving is individually wrapped as a unit, multiple such units making up a single serving) is individually wrapped in any acceptable wrapping known in the art, such as for example, a protective foil wrapping or wax-lined wrapping or the like. In aspects such a protective wrapping can be materially or essentially airtight. In aspects, multiple individually wrapped servings can be further packaged together in, e.g., unit packaging. In aspects, unit packages are provided comprising a number of servings to cover an average dietary plan period of at least about one day, at least about two days, at least about three days, at least about five days, at least about one week, at least about ten days, at least about two weeks, or longer (e.g., at least about one month).

In another aspect, supplementation with between about 10 g and about 100 g can represent between about ½ to about 4 servings of the composition. Also or alternatively, the nutritional composition can be administered in an amount between about 10 g and about 30 g at least one time per day (e.g., at least 2 times per day, at least 3 times per day) and typically no more than 8, not more than 6, not more than 5, or not more than 4 times per day as part of a designed nutritional supplementation plan. In more particular embodiments, the amount of psyllium in one serving of about 20-30 g, about 22-28 g, about 23-26 g, such as about 24 g of NC is between about 3.1 g-4 g, 3.15 g-3.65 g, or 3.2-3.6 g.

Lipid Content, Ingredients, and Components

Nutritional compositions OTI comprise lipids in amounts and/or in ingredients and/or components to afford the composition one, some, most, or all the functional characteristics associated with NCs described herein (e.g., reduced psyllium gelling during mastication, easier manufacturing, etc.). In aspects, the total lipid content of the composition is at least about 25 wt. % of the composition, such as at least about 26 wt. %, at least about 27 wt. %, at least about 28 wt. %, at least about 29 wt. %, or at least about 30 wt. % (e.g., at least about 32 wt. %, 35%, or 38%, or at least about 40 wt. % of the composition is attributable to lipids). In aspects, the total lipid content of NCs is less than about 50 wt. %, less than about 45, 40 wt. %, or 37.5 wt. %, e.g., less than about 35 wt. %, about 33 wt. %, or less than about 31 wt. %.

In aspects, the total lipid content is attributable to the lipid content of the chocolate component, other lipid component, and possibly in part by other ingredients that contain lipids but are not classified as lipid or chocolate ingredients. For example, a chocolate component of a composition can be composed of about 30 wt. % lipids and such chocolate component lipids can, in turn, make up about 20 wt. % of the composition. In aspects, about 40-70 wt. % of the total lipids in the composition can be contributed by (attributed to) the chocolate component, wherein the chocolate component represents between about 50-75 wt. % of the composition and wherein the lipids of the chocolate component represent between about 15-25% of the total lipids in the composition. In aspects, the lipid component (e.g., comprising in aspects cocoa butter, coconut oil, canola oil, and lecithin) can contribute approximately 8-12 wt. % of the total lipids to the composition. In aspects, the lipid component itself represents approximately 8-12 wt. % of the composition, such as approximately 10 wt. % of the composition.

According to some aspects, the ratio of the amount of lipids contributed by the lipid component to the total amount of lipid in the composition ("lipid component lipid:total lipid") is about 1:3-4, such as for example about 1:3, about 1:3.1, about 1:3.2, about 1:3.3, about 1:3.4, about 1:3.5, about 1:3.6, about 1:3.7, about 1:3.8, about 1:3.9, or about 1:4.

In aspects, compositions of the invention can include, e.g., about 25-40 wt. % total lipid content, about 25-35 wt. % lipid, such as about 25-33 wt. % lipid or about 25-32 wt. % lipid, or about 25-31 wt. % lipid, about 28-32 wt. %, or about 29-31 wt. % total lipid content. In aspects, the amount of total lipids in an NC is between 27-38 wt. %. Thus, for example, in a 22-28 g serving, such as a 23-26 g serving, e.g., a 24 g serving, the total lipid content of the serving can range from about 5-10 g, such as, e.g., about 5.5-9.5 g, about 6-9 g, about 6.5-8.5 g, about 7-8 g, about 7.1-7.9 g, or about 7.2-7.5 g.

According to certain embodiments, the amount of psyllium and the amount of total lipid can be present in the compositions of the invention in a ratio (e.g., a total lipid:psyllium ratio) of greater than about 1.5:1, and typically also or alternatively less than about 3.5:1. For example, in embodiments the ratio of total lipid to psyllium is between about 1.6:1 to about 3.2:1, such as between a low-value ratio such as about 1.8:1; about 1.9:1; about 2.0:1, and a high ratio of about 2.2:1, about 2.4:1, about 2.6:1, or about 2.8:1, such as about 3.0:1, 3.2:1, or 3.4:1. In other aspects, the ratio of total lipid:psyllium ratio of a composition of the invention is between about 1.8:1 and 3.4:1, such as 1.9:1 and 3.2:1, e.g., about 1.9:1 to about 3.1:1.

According to some aspects, a nutritional composition can comprise a total fat per single serving representing between about 8-14 Percent Daily Value (% DV) of total fat for a typical person (based on a 2,000 calorie-per-day diet, as recommended by US FDA), such as about 8% DV for total fat, about 9% DV, about 10% DV, about 11% DV, or about 12% DV, such as about 13% DV or about 14% DV for total fat. The terms "total fat" and "saturated fat" are often used when referring to percent daily values as established by regulatory authorities, such as US FDA. When referring to such percent daily values herein, the terms "total fat" and "saturated fat" can be used interchangeably with "total lipids" and "saturated lipids" (each providing implicit support for the other corresponding term). In aspects, when less than a full serving size is consumed, the percent daily value of total fat (total lipid) is adjusted accordingly. For example, in aspects, a single unit can represent a fraction of a serving size (e.g., 1/2 a serving). In such aspects, a single unit can provide approximately 2-9% DV of total fat, such as about 2.5-8.5% DV, about 3-8% DV, or between about 3.5-7.5% of the total fat/lipid DV. In certain aspects, total daily consumption can comprise between, for example, about 2-50% of the daily value of total fat, such as for example between about 3-48% DV total fat, between about 4-46% DV total fat, or for example between about 5-44% DV of total fat, e.g., between about 4-42% DV, between about 5-40% DV, or for example between about 5-36% DV total fat.

Saturated Lipid/Saturated Fat Component/Ingredient(s)

In aspects, nutritional compositions can be characterized based on the saturated lipid content of the composition, which typically is at least predominately, at least materially, or at least essentially saturated lipid.

In one aspect of the invention, saturated lipid is present in the composition in an amount of between about 15-25 wt. %, such as 16-25 wt. %, 16-24 wt. %, 16-22 wt. %, or about 16-21 wt. %, such as, for example, 16-20.5 wt. %, 16-20 wt. %, 16-19.25 wt. %, or 16-18.5 wt. %. Thus, a composition can be characterized in comprising at least about at least about 14 wt. %, at least about 15 wt. %, at least about 16 wt. %, at least about 16.5 wt. %, or at least about 17 wt. %, about 17.5 wt. %, or about 18 wt. % saturated lipid. In some respects, the NC comprises no more than about 20% saturated lipid. In some aspects, the saturated lipid portion of the lipid content of the composition contributed by ingredients other than the chocolate component (e.g., the saturated lipid portion of the non-chocolate lipid ingredients or non-chocolate lipid component) represents between approximately 4-6.5 wt. % of the composition, such as for example between about 4.1-6.4 wt. %, between about 4.2-6.3 wt. %, between about 4.3-6.2 wt. %, between about 4.4-6.1 wt. %, or for example between about 4.5-6 wt. % of the total composition.

In a further aspect of the invention, the total saturated lipid content of a composition, such as a serving, can be present in an amount of about between about 3-6 g, such as, for example, between about 3-4.9 g, 3-4.8 g, 3-4.7 g, 3-4.5 or about 3-4.4 g. According to embodiments, a composition can be characterized in comprising at least about 3.5 g or about 4 g of saturated lipid or at least about 4.1 g, at least about 4.2 g, or at least about 4.3 g of saturated lipid, per every 24 g serving of the composition (which will, in turn, typically comprise 3.1 g-3.9 g, such as 3.15 g-3.75 g, such as 3.2-3.7 g, e.g., 3.4-3.6 g of psyllium).

Nutritional compositions OTI typically comprise one or more ingredients that are classified as fats. The fat composition of the overall composition (total fat) can be contributed, at least in part, by the chocolate component of the composition, as well as a lipid component. A part of a lipid component of a nutritional composition that is composed of saturated lipids can be described as a saturated lipid component. The chocolate component of the composition can also comprise saturated lipids.

In aspects, NCs comprise a fat component, which makes up or is part of a larger lipid component, and that is made up of ingredients characterizable as being solid at room temperature ("fat ingredients") included separately from the chocolate component/ingredients during manufacturing of the composition. The fat content of a composition of the invention typically is made up predominately, materially, essentially, or entirely of fat ingredients in both the fat component and the chocolate component.

In one aspect of the invention, chocolate, ingredients comprising a solid lipid (fat)-rich composition such as, e.g., cocoa butter and coconut oil (comprising both fats and oils), or another additional element (s) of the composition can, in certain aspects, each individually provide sources of saturated lipid content.

In one embodiment at least about 20%, at least about 25%, or at least about 30% of the saturated lipid content of the composition is contributed by one or more ingredients other than the chocolate component/ingredient. In aspects, at least about 20 wt. %, at least about 25 wt. %, at least about 26 wt. %, at least about 27 wt. %, at least about 28 wt. %, at least about 29 wt. %, or at least about 30 wt. % of the saturated lipid content of the composition is contributed by the lipid component. In aspects, at least about 20%, at least about 25%, at least about 30%, at least about 40%, at least about 50%, at least about 60%, or at least about 70%, such as at least about 80%, at least about 90%, or even at least 95% of the saturated lipid not contributed to the composition by the chocolate ingredient is attributable to one or more ingredients that most of which, materially all of which, essentially all of which, or all of which can typically be characterizable as a solid at room temperature. In aspects such components are part of the lipid component. In aspects such components are part of the fat component of the lipid component.

A fat component can comprise any suitable one or more fat ingredients or fat-containing ingredients (e.g., a composition or combination of such compositions). Examples of fat ingredients that can be incorporated in the nutritional product include cocoa butter, shortening, stick margarine, hydrogenated and partially hydrogenated oils, coconut oil, palm and palm kernel oils, and beef fat.

In aspects, at least about 2 wt. % of the composition, such as at least about 3 wt. %, at least about 4 wt. %, or at least about 5 wt. %, such as even at least about 6 wt. %, or at least about 7 wt. % of the composition is attributed to one or more solid lipid ingredients, solid-lipid-rich ingredients, or both, such as cocoa butter and/or coconut oil, which make up at least part of the fat component and which contribute to the total fat of the composition. In aspects, the fat component contributes about 20-30 wt. %, such as about 21-29 wt. %, about 22-28 wt. %, or about 23-26 wt. % of the total fat. In aspects, about 2-10 wt. %, about 2-9 wt. %, or about 2-8 wt. %, such as about 4-10 wt. % or about 6-10 wt. %, or for example between about 5-8 wt. % or about 6-8 wt. % or about 7-8 wt. % of the composition can be attributed to one or more solid lipid or solid-lipid-rich ingredients in a fat component.

According to certain embodiments, the amount of solid fat in the lipid component, is at least predominately contributed by, is at least materially contributed by, or is at least essentially contributed by, or is entirely contributed by cocoa butter. In one embodiment, cocoa butter accounts for about 4-10 wt. % of a composition, such as for example between about 5-10 wt. %, or for example between about 6-10 wt. %, such as between approximately 4-9 wt. %, between approximately 4-8 wt. %, between approximately 5-9 wt. %, between approximately 5-8 wt. % or between about 6-8 wt. %, as in for example about 7 wt. %, of the composition. In a certain embodiment, the formulation used to make the composition comprises about 6-8 wt. % cocoa butter, not including any cocoa butter present in a chocolate ingredient of the composition.

According to certain embodiments, the amount of psyllium and the amount of saturated lipid can be present in the compositions of the invention in a saturated lipid to psyllium ratio of about 1:1. In aspects, the saturated lipid to psyllium ratio is greater than 1:1, e.g., greater than 1.1:1 or 1.2:1 or that is typically less than about 2:1, such as less than about 1.8:1 or less than about 1.5:1. According to examples of such embodiments the amounts of saturated lipid and psyllium are such that the ratio between these components of the composition is between 1:1 to 2.2:1, such as about 1:1-2.1:1, about 1:1 to about 2:1, about 1:1 to about 1.8:1, about 1:1 to about 1.7:1; about 1:1 to about 1:1; or about 1:1 to about 1.5:1 or about 1.1:1-1.4:1.

In some aspects, the total lipid to total saturated lipid ratio of an NC can be between 1-2.5:1, such as between 1.1-2.4:1, or between 1.2-2.3:1. In some aspects, the total lipid to total saturated lipid ratio of a nutritional composition can be about 1.2:1, about 1.3:1, about 1.4:1, about 1.5:1, about 1.6:1, about 1.7:1, about 1.8:1, about 1.9:1, about 2:1, about 2.1:1, about 2.2:1, about 2.3:1, about 2.4:1, or about 2.5:1.

According to some aspects, the ratio of the chocolate component (e.g., the total chocolate component, not exclusive of the lipids of the chocolate component) to total saturated lipids, can be between about 2-4.5:1, such as for example between about 2.1-4.4:1, between about 2.2-4.3:1, between about 2.3-4.2:1, or between about 2.4-4.1:1, such as between about 2.5-4.2:1, or for example between about 2.6-4.1:1.

According to certain aspects, the nutritional composition can comprise a total saturated lipid per serving representing between about 18-22 percent Daily Value (% DV) of total saturated fat, such as about 18% DV, about 19% DV, about 20% DV, about 21% DV, or about 22% DV saturated fat/lipid. In aspects, when less than a full serving size in consumed, the percent daily value of saturated fat is adjusted accordingly. For example, in aspects, a single unit can represent a fraction of a serving size (e.g., 1/2 serving). In such aspects, a single unit can provide between approximately 6-14% DV of saturated fat, such as for example between about 6.5-13.5% DV, between about 7-13% DV, or for example between about 7.5-12.5% DV of saturated fat. In certain aspects, total daily consumption can comprise between, for example, about 5-75% daily value of total saturated fat, such as for example between about 6-74% DV total saturated fat, between about 7-73% DV total saturated fat, or for example between about 8-72% DV, such as between about 9-70% DV, between about 10-65% DV, or for example between about 10-60% DV total saturated fat. Typically, the total daily consumption means an amount recommended for consumption in a day. In aspects, the total daily consumption can vary between at least two periods (e.g., increasing by 1.5-9 times, such as 2-6 times in a second period after an initial lower consumption period). In aspects, a consumer's daily consumption can vary, but the average of the consumer's daily consumption over a period of frequent/ regular use (e.g., about 1 week, about 1-4 weeks, or about 1-3, 1-36, 1-60, or 1-120 months) will be approximately equivalent to the recommended total daily consumption or will not significantly differ from the total daily consumption.

Unsaturated Lipid Component/Ingredients

In another aspect of the invention, the composition also or alternatively can be characterized based on unsaturated lipid content, unsaturated lipid ingredients, or both. In exemplary aspects, compositions of the invention can be characterized based on having an unsaturated lipid content in an amount of between about 5-20 wt. %, such as about 5-20 wt. %, such as about 10-20 wt. % or 5-18 wt. %, e.g., about 5-16 wt. %, about 5-14 wt. %, or about 10-15 wt. %, such as, for example, 10-14 wt. %, 11-14 wt. %, or for example about 12 wt. %. Thus, for example, the unsaturated lipid content in a composition of about 22-28 g, such as 23-26 g, e.g., 24 g, can be in the range of about 2.4-4.8 g, such as, for example, between about 2.4-4.6 g per 24 g, 2.4-4.4 g per 24 g, 2.4-4.2 g per 24 g, or 2.4-4 g per 24 g. According to embodiments, such a 24 g bar or other 24 g serving size of a composition of the invention will contain at least 2 g, at least 2.5 g, at least 3 g, at least 3.1 g, or at least 3.2 g of unsaturated lipid, such as 2.5-4 g unsaturated lipid, 2.6-3.5 g unsaturated lipid, or 2.8-3.2 g of unsaturated lipid per 24 g serving size.

In another aspect, nutritional compositions can be characterized by the amount of oil used in making the composition, contained in the final composition, or that the composition absorbs in certain contexts. Oil ingredients may be predominately composed, materially composed, essentially composed, or entirely composed of one or more oils. For example, canola oil comprises both fats and oils. Because canola oil at room temperature is a liquid, it is considered an oil. Other oils that can be incorporated in a lipid component include soybean oil, sunflower oil, olive oil, or vegetable oils (however, partially hydrogenated vegetable oils are fats). In aspects, one or more lecithins may be added to the composition as a liquid, lipid-rich ingredient and considered an oil. In aspects, lecithin content may contribute to total lipid, total oil, total fat, total saturated lipid (saturated lipid), or total unsaturated lipid (total unsaturated lipid) content of the composition, or any combination thereof. In aspects, lecithin further acts as an emulsifier, and in this respect the lecithin may vary from the characteristic nature of any one or more other oils in the composition, such as canola oil, e.g., in its amphiphilic properties.

Emulsifiers, such as one or more lecithin ingredients, can be present in the chocolate component, outside of the chocolate component (e.g., in an emulsion component/lipid component), or both. In parts of this disclosure, lecithin outside of the chocolate component is described with respect to being an emulsifier and in other parts is described or included as an oil. Typically, such descriptions are in reference to a single amount of lecithin outside of the chocolate component (e.g., a passage may describe compositions comprising about 0.1 wt. % lecithin as an oil and about 0.1 wt. % lecithin as an emulsifier, but such compositions typically comprise only 0.1 wt. % lecithin).

In aspects, oil ingredients account for less than about 3 wt. %, e.g., less than about 2.8 wt. %, less than about 2.6 wt. %, less than about 2.4 wt. %, less than about 2.2 wt. %, or less than about 2.1 wt. % of an NC.

According to some aspects, the ratio of saturated fat to unsaturated fat in an NC of the invention is greater than 1:1. For example, in aspects the ratio of total saturated fat in the NC to the total unsaturated fat in the NC is about 1.1:1, about 1.2:1, about 1.3:1, about 1.4:1, about 1.5:1, about 1.6:1, about 1.7:1, about 1.8:1, or about 1.9:1. In some aspects, the ratio of saturated fat to unsaturated fat in an NC is less than 2:1.

In certain aspects, NCs of the invention comprise a ratio of the amount of unsaturated lipid contributed by ingredients other than the chocolate component (saturated lipid contributed by "non-chocolate lipid ingredients") to total unsaturated lipid of the composition of between about 3:1-3.2:1, such as about 3.05:1, 3.1:1, or about 3.15:1.

Reduction of Psyllium-Associated Negative Properties

In aspects, the psyllium-containing fiber component of the composition, when combined with the lipid and flavoring/chocolate components in the amounts and having the characteristics described herein, detectably or significantly reduces one or more psyllium-associated consumption adverse effects, psyllium-associated manufacturing adverse effects, or both. Examples of the psyllium associated adverse effects that are reduced in compositions of the invention are described in the following paragraphs, as well as in other portions of this disclosure.

In aspects, compositions of the invention are associated with a detectable or significant reduction in the frequency, degree, or duration of the generation of a filmy, slippery, or slimy mouth feel during consumption as compared to one, some, most, or all of the products of the prior art (e.g., Metamucil® powder, Metamucil® wafers, or both). Such mouth feel is believed to be caused by the hydration of psyllium within the mouth and throat upon consumption before swallowing, (e.g., during mastication), or while swallowing, causing the psyllium to gel, creating an unpleasant coating or negative taste on the surface of oral mucosal layers of the mouth or throat. Such hydration of psyllium powder products can occur upon mixing of psyllium with water or water-based products prior to consumption/in preparation for drinking, prior to the product even entering the mouth.

According to one aspect of the invention, the psyllium component of the composition (in the composition) does not absorb more than about 5%, such as more than about 7.5%, such as more than about 10%, such as more than about 15%, such as more than about 20 wt. %, more than about 25%, or more than about 33% of the psyllium's water-holding capacity during the average mastication and swallowing time for the product (e.g., as determined by a suitable trial or suitable approximation test). Thus, for example, compositions of the invention can be characterized in the psyllium of the composition not absorbing more than about 18%, not more than about 16%, or not more than about 14%, or not more than about 12%, or not more than about 10% of its water holding capacity while in the mouth, e.g., during mastication, or throat, e.g., during swallowing, of a consumer.

In one aspect, nutritional compositions or the fiber/psyllium component thereof does not absorb more than 10%, 15%, 20%, 25%, or 33% of its water holding capacity during mastication and swallowing in a significant proportion of users, in most users, or on average.

In aspects, consumption of compositions of the invention are associated with a detectable or significant reduction in incidence of choking, gagging, or coughing as compared to one or more on-market psyllium products, such as Metamucil® wafers or powder.

In aspects, nutritional compositions of the invention are on average, in significant amount, or predominately are deemed more palatable than Metamucil® products, such as Metamucil® wafer or powder products.

In some aspects of the invention, the lipid-rich composition, e.g., by manner of incorporating a significant concentration of lipid(s) (e.g., establishing a concentration of total lipids in the composition which is greater than 25 wt. %, such as greater than 30 wt. % lipids), detectably or significantly protects the psyllium from hydration prior to completion of swallowing so as to prevent significantly negative organoleptic experiences for a significant number of consumers (e.g., as measured by consumer testing of an adequate population of consumers). In aspects, the psyllium is surrounded by, or agglomerated within, the high concentration of lipids, starch complexes, or a combination of lipids and starch complexes to aid in the protection of psyllium from hydration. In aspects, at least sizeable, at least predominate, or at least material amounts of psyllium are protected from hydration during normal mastication by the lipids, starch/starch complexes, or a combination of lipids and starch/starch complexes used to make the composition.

In aspects, an emulsion component comprises a starch component, e.g., at least one starch such as cornstarch, e.g., in about 1-7 wt. % of the total composition, e.g., in about 2-6 wt. % of the total composition, e.g., 2-5 wt. %, 2-4 wt. %, 3-5 wt. %, or 3-4 wt. % of the composition. In aspects, the starch component of an emulsion detectably or significantly aids in the protection of psyllium from hydration. In aspects one or more starches or starch complexes are present in the composition and are capable of detectably or significantly aiding in the protection of psyllium from water exposure until the psyllium is beyond a point in the digestive tract where a consumer experiences the negative organoleptic properties of psyllium gelation due to water absorption. In aspects, a starch or starch complex is or can be any kind of starch or starch complex such as that of cornstarch, arrowroot starch, tapioca and potato starch, rice starch, or other known starches in the art. In aspects, the starch is a cornstarch or a cornstarch complex. In aspects, cornstarch is an element of the emulsion component described elsewhere herein.

According to certain embodiments, a composition of the invention, such as a bar formed from a composition of the invention, is capable of materially, essentially, or entirely maintaining its structure when completely immersed in water or other aqueous liquid for a period of about 20 minutes or more, about 30 minutes or more, or even up to about 45 minutes or longer (e.g., about 1 hour or longer). That is, according to certain aspects, less than 20%, such as less than about 18%, less than about 16%, less than about 14%, less than about 12%, less than about 10%, less than about 8%, less than about 6%, or for example less than about 4% of the product deteriorates, or, also or alternatively, the psyllium of the product does not absorb more than approximately 25%, more than approximately 20%, more than approximately 15%, more than approximately 10%, or more than approximately 5% of its total water holding capacity so as to cause detectible or significant expansion of the psyllium (e.g., swelling), gelation of the psyllium, or a combination of the two after being completely immersed in an aqueous environment after about 5 minutes, after about 10 minutes, after about 15 minutes, after about 20 minutes, after about 25 minutes, after about 30 minutes, after about 35 minutes, after about 40 minutes, or after about 45 minutes.

In some aspects, the composition, when completely immersed in an aqueous environment, maintains at least 50% of the fiber component in its non-hydrated state (e.g., its finished product state) for up to 45 minutes, such as, for example, at least about 50%, at least about 55%, at least about 60%, at least about 65%, at least about 70%, at least about 75%, at least about 80%, at least about 85%, at least about 90%, or at least about 95% of the fiber in the immersed finished product is maintained in its finished product state (e.g., has not absorbed water from the aqueous environment sufficient to cause significant structural changes in the finished product) after being immersed in water for about 5 minutes, about 10 minutes, about 15 minutes, about 20 minutes, about 25 minutes, about 30 minutes, about 35 minutes, about 40 minutes, or for example after about 45 minutes of water immersion.

In aspects, the psyllium of the composition, when combined with the lipid and chocolate components in the amounts and having the characteristics described herein, also or alternatively is protected from hydration during manufacturing (e.g., does not absorb more than about 10 wt. %, about 20 wt. %, or about 25 wt. % of its water holding capacity). In aspects, the psyllium of the composition, when combined with the chocolate and lipid components of the composition, does not change viscosity during manufacture to a degree that a significant amount of expense is incurred, delay is incurred, or product lost during manufacturing. of the product negatively affecting the manufacturing process). In aspects, the mix of at least psyllium, chocolate, and lipid ingredients used to form the composition is such that the final composition can be prepared using standard food equipment, examples of which are provided below.

"Chocolate" Component

Nutritional compositions typically comprise a chocolate component or a flavoring component having similar properties to a chocolate component (e.g., about a similar amount of total lipids, saturated lipid, sugar, and non-saturated lipid).

In one aspect, a chocolate/flavoring component has an at least sizable lipid content (e.g., is at least about 25% or at least about 30% lipid).

In one aspect, the chocolate/flavoring component at least predominately, at least materially, at least essentially, or entirely is composed of a chocolate component, comprising one or more chocolate ingredients. Chocolate ingredients typically comprise a mixture of ingredients used to form the chocolate, such as cocoa butter, cocoa/cacao, sugar, milk solids, an emulsifier (e.g., lecithin), and other components.

In aspects, an NC can comprise two or more chocolate/flavoring components, such as comprising two or more chocolate components (for example but not limited to a white chocolate and a milk chocolate component).

According to one embodiment, NCs comprise at least about 50 wt. % of a chocolate/flavoring component. In aspects, the flavoring component also or alternatively is at least substantially homogeneously or homogenously dispersed through the nutritional composition. In aspects, no portion of an NC, such as a bar/serving, of 25% or more of the NC (by weight, area, or both) differs by more than 50%, more than 40%, more than 30%, more than about 20%, more than about 15%, or more than about 10% in terms of the amount of flavoring component (and possibly other components) from any other area/portion of the NC of similar or greater measurement(s).

In aspects, the chocolate/flavoring component is a sizable component, or the predominant component of the NC and, accordingly, can be referred to as the "base component" or "base." Any description of a chocolate/flavoring component or a base component here can be interchanged and each term/element implicitly provides support for the other, despite the inclusion of several passages in which both are separately mentioned.

In aspects, NCs comprise a chocolate base, such as a dark chocolate, a milk chocolate, or a white chocolate base. Although other ingredients/components can contribute to the overall flavor of the composition, such as cocoa butter, the chocolate/flavor component is typically the component that provides the primary flavor of the composition, such as cocoa, e.g., cocoa solids. In the case of a white chocolate base, for example, the mixture of components that define a white chocolate flavor define the primary flavor.

In aspects, the flavoring/base component can comprise a standardized chocolate. In aspects, the flavoring/base component can comprise a compound coating chocolate. As used here, a standardized chocolate is a chocolate that meets United States Food and Drug Administration (US FDA) chocolate standards, and can apply to, e.g., a milk chocolate, a sweet, semisweet, or bittersweet chocolate, or white chocolates or meets the industry recognized definition of a dark chocolate. In aspects, a compound coating chocolate or compound coating white chocolate, known in the art, may be suitable if such a compound coating chocolate were to meet the characteristics described herein. In aspects, a compound coating milk chocolate, a compound coating semisweet chocolate, a compound coating bittersweet chocolate, a compound coating white chocolate, and the like may be incorporated. In aspects, a standardized chocolate or compound chocolate coating can comprise artificial sugar or non-sugar substitute sweeteners.

According to one embodiment, the flavoring/base component of the nutritional composition is at least predominately, at least materially, at least essentially, or is entirely hydrophobic. According to embodiments, a flavoring component, such as a base component, is at least about 15 wt. %, at least about 20 wt. %, at least about 25 wt. %, at least about 33 wt. %, at least about 40 wt. %, or at least about 50 wt. % comprised of one or more lipids, e.g., about 15-40 wt. %, such as about 17.5-35 wt. % of the flavoring component is composed of one or more lipids. According to embodiments, at least about 10%, at least about 15%, at least about 20%, or at least about 25% of a flavoring/base component also or alternatively is composed of saturated lipid (e.g., at least about 12.5-25% of a flavoring composition is saturated lipid). In aspects, the ratio of the wt. % of the composition represented by the flavoring component (e.g., the chocolate component/base) to the wt. % of the total saturated lipid content of the composition is greater than 2:1, such as greater than about 2.5:1, greater than about 3:1, greater than about 3.2:1, greater than about 3.5:1, or greater than about 4:1, such as greater than about 4.3:1.

In aspects, the ratio of the amount of lipids contributed to the composition by the chocolate component to the amount of lipids contributed to the composition by ingredients other than the chocolate component (e.g., by the lipid component), is between about 0.75:1-3.25:1, such as for example between about 0.85:1-3.15:1, between about 0.95:1-3.05:1, between about 1.05:1-2.95:1, between about 1.15:1-2.85:1, or for example between about 1.25:1-2.75:1 or between about 1.5:1-3:1, such as between about 1.5:1-2.75:1 or for example between about 1.75:1-2.75:1, such as between about 1.75:1-2.5:1.

In aspects, the nutritional composition can be described by a three-part ratio between the amount of lipid contributed to the NC by the flavoring component (e.g., the chocolate component/base), the amount of total lipid in the NC, and the amount of lipid contributed to the NC by the lipid component. In aspects, the ratio of the total amount of lipids in the composition contributed by the flavoring component (e.g., the chocolate component/base)—to—the total amount of lipids in the composition—to—the amount of lipid contributed to the NC by the lipid component ("chocolate lipid:total lipid:lipid component lipid") is <3: <4:1, such as 1-3:2-4:1, such as e.g., about 2:3:1.

In aspects, the flavoring component or base of the composition of the invention is a dark chocolate composition, a milk chocolate composition, or a white chocolate composition. Other ingredients or ingredient mixtures, with or without additional flavorings, also or alternatively can be used to provide a base component for a composition of the invention. In one embodiment, the composition comprises a chocolate base and one or more other flavorings, which can be blended or separate from one another. Thus, for example, a composition of the invention can be a bar comprising a chocolate base component and an accompanying flavor component such as vanilla, strawberry, peanut butter, fruit, caramel, yogurt, and the like. According to embodiments, the composition is at least predominately composed of a chocolate base component.

In aspects, a chocolate flavoring component/base component of a composition can be a white chocolate, a milk chocolate, or a dark chocolate. According to certain aspects, a chocolate base is a milk chocolate. In further embodiments, the chocolate base is a dark chocolate. According to alternative aspects, the chocolate base is a white chocolate.

In aspects, a flavoring component, such as a chocolate component, can be sugar-free flavoring, such as a sugar-free chocolate (e.g., according to US FDA or similar regulatory body definitions thereof). In aspects, such a product is used as part of a dietary management by users with blood sugar conditions, such as diabetes. In other, related aspects the entire nutritional composition can be characterized as low in sugar or sugar-free, e.g., containing no more than 0.5 grams of monosaccharides and disaccharides.

Typically the term chocolate herein means any of dark chocolate, milk chocolate, or white chocolate, though dark chocolate and milk chocolate represent in some respects separate aspects of the invention from compositions comprising white chocolate or other flavorings, and each represent unique aspects of the invention. The term should thus be understood to provide support for all three aspects, collectively and independently, unless otherwise stated or clearly indicated by context.

In one exemplary embodiment, a base component of nutritional compositions is a white chocolate base component, which typically will comprise at least about 20 wt. % cocoa butter and at least about 3.5 wt. % milk fat, typically with at least about 14 wt. % milk solids, and typically comprises at least about 28 wt. % total lipid (e.g., about 28-35 wt. % total lipid) and optionally at least about 16 wt. % saturated lipid, such as about 16-25 wt. % saturated lipid, and optionally comprising at least about 50 wt. % sugar, such as at least about 55 wt. % sugar. According to 21 C.F.R. § 163.124, white chocolate comprises not less than 20% by weight of cacao fat, not less than 3.5% by weight of milk fat, and not less than 14% by weight of total milk solids (including dairy ingredients such as cream, milk fat, butter, milk, dry whole milk, concentrated milk, evaporated milk, sweetened condensed milk, skim milk, concentrated skim milk, evaporated skim milk, sweetened condensed skim milk, nonfat dry milk, concentrated buttermilk, dried buttermilk, and malted milk), and not more than 55% by weight of one or more optional nutritive carbohydrate sweeteners.

In aspects, the chocolate used in the compositions of the invention meets the United States' requirements or standards for white chocolate.

According to embodiments, the flavoring component/base of the nutritional composition is at least predominately, at least materially, or at least essentially made up of one or more cacao-associated chocolate ingredients or is entirely composed of chocolate(s). The term "chocolate" here typically is a reference to cacao-associated chocolate components/ingredients (milk chocolate or dark chocolate ingredients/components).

A chocolate ingredient used as an ingredient, component, or base of the nutritional composition can be a standardized or compound coating milk chocolate, semi-sweet chocolate, bittersweet chocolate, dark chocolate, white chocolate, or any combination of one or more of these chocolate types. In aspects, a chocolate of the NC is a sugar-free chocolate.

In one embodiment, the chocolate of a composition is characterizable as a milk chocolate, as recognized by a regulatory authority, e.g., US Food and Drug Administration (FDA). According to 21 C.F.R. § 163.130, for example, "milk chocolate" comprises not less than 10% by weight of chocolate liquor, (prepared by finely grinding cacao nibs and containing between 50% by weight and 60% by weight of cacao fat), not less than 3.39% by weight of milk fat, not less than 12% by weight of total milk solids (including dairy ingredients such as cream, milk fat, butter, milk, concentrated milk, evaporated milk, sweetened condensed milk, dried milk, skim milk, concentrated skim milk, evaporated skim milk, sweetened condensed skim milk, or nonfat dry milk), and one or more optional nutritive carbohydrate sweeteners. In aspects, a chocolate ingredient/component of NCs, e.g., the flavoring component/base, meets the United States' FDA requirements or standards for milk chocolate.

The term "dark chocolate," typically refers to plain or milk chocolate which is produced using a higher percentage of cocoa/cacao than milk chocolate (e.g., at least 15% chocolate liquor, such as 15% to 34%, and in some cases as high as 50% or more, 60% or more, 70% or more, or even 80% or more) According to 21 C.F.R. § 163.123(a)(2), semisweet chocolate or bittersweet chocolate are types of sweet chocolate that contains not less than 35 percent by weight of chocolate liquor. In the industry, semisweet and bittersweet chocolate are chocolates that are often referred to as dark chocolate. In one embodiment, the chocolate of a composition is characterizable as a dark chocolate. In aspects, a chocolate ingredient/component of NCs, e.g., the flavoring component/base, meets recognized standards for dark chocolate.

In aspects, a chocolate component makes up more than 50 wt. % of the nutritional composition. According to aspects, a chocolate component makes up at least about 52 wt. % of an NC, e.g., at least about 53.5 wt. %, at least about 55 wt. %, or at least about 57.5 wt. % of an NC. In aspects, a chocolate component makes up at least about 60 wt. % of an NC, e.g., an NC comprises at least about 62.5 wt. % chocolate, at least about 65 wt. % chocolate, or at least about 67 wt. % chocolate. In aspects, a nutritional composition also or alternatively comprises less than about 80 wt. %, less than about 77 wt. %, less than 75 wt. %, less than 72.5 wt. %, less than 70 wt. %, less than 67.5 wt. %, or less than 66.6 wt. % chocolate.

In aspects, a nutritional composition comprises about 45-80 wt. % chocolate (which can be made up of one or more types of chocolates), e.g., about 47.5-77.5 wt. %, about 50-75 wt. %, about 50-70 wt. %, or about 50-65 wt. % chocolate. In specific exemplary aspects, an NC comprises 52-69 wt. % chocolate, such as 53-69 wt. % chocolate, such as 54-68 wt. % chocolate, e.g., 55-65 wt. % chocolate, such as about 55 wt. %, about 56 wt. %, about 57 wt. %, about 58 wt. %, about 59 wt. %, about 60 wt. %, about 61 wt. %, 62 wt. %, about 63 wt. %, about 64 wt. %, or about 65 wt. %, about 66 wt. % or about 67 wt. % chocolate. In one embodiment, the composition comprises less than about 69 wt. %, such as less than 68.5 wt. % or less than 68 wt. % chocolate. In other embodiments, the composition comprises more than 50 wt. % chocolate, more than 52.5 wt. % chocolate, more than 57.5 wt. % chocolate, or more than 59 wt. % chocolate.

In exemplary single-serving finished products comprising about 24-30 g of NC, for example about 24 g, or about 25 g, or about 26 g, or about 27 g, or about 28 g, or about 29 g, or about 30 g of NC, at least about 10 g of the nutritional composition can be from one or more chocolate ingredients. In more particular/alternative aspects, at least about 11 g, at least about 12 g, at least about 13 g, at least about 14 g, at least about 15 g, at least about 16 g, at least about 17 g, or at least 18 g of any such composition is composed of chocolate. These amounts may, of course, be adjusted to accommodate smaller serving sizes, such as snack-size compositions, bite-size compositions (about 2 g-12 g, such as about 3 g-9 g or about 2.5 g-10 g), etc., exemplified elsewhere herein. In a particular exemplary embodiment, the invention provides a composition in the form of a 24 g finished bar product containing between about 10-18 g of chocolate, such as between about 11-18 g of chocolate, or about 11-17 g of chocolate, such about 11-16 g of chocolate, or such as about 12-15 g of chocolate.

In an additional aspect, the ratio of chocolate component to psyllium of an NC is at least about 3:1, such as for example at least about 3.2:1 or at least about 3.5:1 to a maximum ratio of about 6:1 such as about 5:1 or about 5.5:1. In more particular aspects, compositions of the invention can be characterized in having a chocolate component to psyllium ratio of about 2-6:1; such as about 3-5.5:1; or, more particularly in some embodiments about 3.5-5.5:1.

Texturizing Element/Component (Ingredients)

In another aspect, nutritional compositions comprise a texturizing element (a texturing component). A texturizing element can be any consumable ingredient or mixture of ingredients detectably or significantly differing in texture from the main components of the composition (e.g., the chocolate, lipid, and psyllium components). The texturizing component detectably modifies the texture, e.g., the crunchiness, of the composition. In aspects, the texturizing element also can contribute to the flavor of the composition, can increase the feeling of satiety, can add to the overall experience and enjoyment of the composition, can add to the nutritional content of the composition, or provide/perform any combination thereof. In aspects, the texturing element detectably changes the sound experience of eating the composition for a significant number of users, an average user, or a majority of users. In aspects, the texturizing element detectably or significantly enhances adoption, continued use, or satisfaction with the NC.

In certain aspects, the psyllium of the composition can provide a texture to an NC, such that it provides a perceptible or noticeable crunch or sound experience to the composition in finished product form. In aspects, some, most, materially all, or at least essentially all of the psyllium is present in the composition having an average mesh size such that the psyllium ingredient does not provide a perceptible or noticeable crunch or sound experience to the final product, and any perceptible or noticeable crunch, sound experience, or significantly altered texture (e.g., perceivable by visual observation) is provided by a component other than psyllium, such as one or more ingredients as described below. In certain aspects, the texturizing element is not psyllium.

In aspects, the texturizing aspect can be, for example, but not limited to, a nut (nuts), a candy (including a toffee or a brittle), a dried fruit, or a dried grain. In other embodiments, the texturizing component comprises a protein crisp. In still other aspects, the texturizing component comprises chia seeds. According to some aspects of the invention, the composition comprises a crunchy element in the form of a crisp grain. A "crisp grain" refers to a grain after it is subjected to any process sufficient to make the grain "crunchy," such as extrusion, drying, toasting, frying, or another similar method. The crisp grain can be any crisp grain sufficient to provide a pleasant and satiating experience such as rice (e.g., a puffed or otherwise crispy rice, "puffed rice" being included by the term "crispy rice" as used herein), toasted rolled oats, flaked oats, cornmeal, wheat, barley, rue corn, quinoa, sorghum, or other types of grain. In some aspects, texture can be provided by a plurality of texturizing elements. In aspects, texture can be provided/supplemented by a single texturizing element, e.g., a crisp rice such as a puffed rice. In aspects, a crisp rice is the only texturizing agent in the composition or comprises a material amount or essential amount thereof.

In one aspect of the current invention, the crisp grain is crisp rice (e.g., a puffed or otherwise crispy rice). In a further aspect of the invention, the crisp rice is present in an amount of at least about 5 wt. %, e.g., at least about 7 wt. %, e.g., at least 8 wt. % or at least 10 wt. %. In aspects, the composition includes 5-20 wt. %, 6-16 wt. % or 6-18 wt. %, or 5-15 wt. % of a texturizing component, such as crisp rice. According to exemplary embodiments, compositions can include about 5 wt. % to about 10 wt. %, such as about 5 wt. % to about 9 wt. %, or about 5 wt. % to about 8 wt. % of a texturizing component, such as a crisp rice.

In a further aspect of the invention, the crisp rice or alternative texturizing element has a density measurement such that the individual particles of the texturizing element, e.g., the individual rice pieces, are distributed throughout the composition in an approximately equal distribution or similar distribution resulting in a substantially homogeneous composition with respect to the texturizing element. In aspects, the texturizing element, such as the crisp rice, has a density which provides to at least a significant number of consumers or an average consumer a detectible crunch upon consumption as a component in the final product. In aspects, the density of the of the texturizing element is sufficient to prevent significant breakdown during manufacturing, such as e.g., sufficient breakdown such that the texturizing element is no longer capable of providing the desired crunch upon consumption to a significant number of consumers or an average consumer.

In aspects, the density of the crisp rice or alternative texturizing element used in compositions of the invention is at least about 0.1 g/cm$^3$ (g/cc), e.g., at least at least 0.1 g/cm$^3$, at least about 0.15 g/cm$^3$, at least about 0.175 g/cm$^3$, or at least about 0.2 g/cm$^3$ (g/cc). In aspects, the crisp rice or other texturizing element has a density of at least about 0.225 g/cm$^3$, at least about 0.25 g/cm$^3$ (g/cc), at least about 0.275 g/cm$^3$ (g/cc), at least about 0.28 g/cm$^3$ (g/cc), at least about 0.3 g/cm$^3$ (g/cc), or such as for example at least about 0.35 g/cm$^3$ (g/cc). In still other aspects, the texturizing component has a density of about 0.1-0.8 g/cc, e.g., about 0.15-0.75 g/cc, about 0.2-0.8 g/cc, about 0.2-0.75 g/cc, or about 0.2-0.7 g/cc, e.g., about 0.25-0.75 g/cc. In aspects, the density of the crisp rice or alternative texturizing element used in compositions of the invention is less than 0.8 g/cc.

In a further exemplary embodiment, a nutritional composition can comprise a crisp protein in addition to, or in replacement of, a crisped grain. A crisp protein component can comprise any crisp protein(s) sufficient to provide a pleasant and satiating experience such as soy, whey, milk, pea, rice, peanut, hemp, or egg proteins. Such a crisp protein can, in aspects, confer a health benefit. Similar considerations concerning density should be taken for crisp protein or other texture-enhancing ingredients incorporated into the composition as those made for the embodied crisp rice, can apply, such as where the composition is characterizable as a substantially homogeneous formulation wherein the texture-adding component is at least substantially uniformly distributed in the final product and is capable of providing a detectible and suitable crunch upon consumption as described elsewhere herein.

In some respects, a non-homogeneous bar/NC may be preferable. That is, a final product comprising an area representing about 25% of a final product (e.g., a bar) differing from another area representing about 25% of a final product in content of an, e.g., texturizing element or one or more other components by more than 10%, 15%, 25%, 33%, or 50% may be preferable. For example, a bar composition can have layers, portions, fillings, and the like, with different characteristics. In such cases, the density of an incorporated texture enhancing element, such as a crisp grain (e.g., a crisp rice), or also or alternatively a crisp protein can be less restrictive, such that an intentionally non-homogeneous composition is formed, such as for example, a fiber-containing, (e.g., a psyllium-containing) chocolate-based bar, cookie, or other food product having a layer of crispy texture which is distinct from the main body of the food product.

Other Possible Ingredients and Compositional Characteristics

Water Content

In another aspect, nutritional compositions also or alternatively are produced using no water. In other embodiments, the composition also or alternatively comprises no detectable amount of water such that any water present in the composition is present in an amount undetectable by standard techniques used in the art. In some aspects, water can be present in an amount within the compositions described herein which is less than about 1%, such as less than about 0.9 wt. %, less than about 0.8 wt. %, less than about 0.7 wt. %, less than about 0.6 wt. %, less than about 0.5 wt. %, less than about 0.4 wt. %, less than about 0.3 wt. %, less than about 0.2 wt. %, or less than about 0.1 wt. %; such as less than about 0.05 wt. %; such as less than about 0.025 wt. %; such as less than about 0.01 wt. %, or for example in an amount less than about 0.005 wt. % or less.

Sweeteners

According to further embodiments, the nutritional composition can comprise one or more sweeteners. The one or more sweeteners can be any edible (e.g., safe for consumption) sweetener(s) capable of improving the flavor of the composition. In some embodiments, one or more sweetener(s) can comprise one or more types of sugar or sugar substitutes such as glucose, fructose, corn syrup, high-fructose corn syrup, sugar alcohols, aspartame, sucralose, stevia, saccharin, and the like. Alternatively, according to certain embodiments, no sweetener is added. In another embodiment, any sweetener added to the composition comprises a sugar-free sweetener. In another embodiment, the composition is sugar-free, containing no added sugar or sweeteners, and is suitable for sugar-sensitive consumers, especially diabetic consumers who are required to maintain strict, low levels of sugar intake. Specifically, in aspects, the composition meets US or US FDA definitions for labeling as a sugar-free, low-sugar, or reduced sugar product. According to 21 C.F.R. 101.60 (as published in 2020), a sugar-free-labeled product contains less than 0.5 g of sugar (typically monosaccharide and disaccharide) per labeled serving. In certain aspects of the invention, the composition contains less than about 0.5 g of sugar, such as less than about 0.4 g of sugar, such as less than about 0.3 g of sugar, such as less than 0.2 g of sugar, such as less than 0.1 g of sugar. Such products may, for example, be characterizable as including ingredients that add a "negligible amount" of sugar, for example. In some aspects, sugar substitutes are included in the formulation of the composition, such as saccharin, sucralose, aspartame, advantame, neotame, acesulfame K, or a combination of two or more thereof, or any other suitable sugar substitute means known in the art.

Emulsifier Component and Emulsion Component

In one aspect, an emulsion of some components/ingredients is formed and such an emulsion component is used as a component in the manufacture of NCs and mixed as a single ingredient with other components, such as the fiber/psyllium component, chocolate component, and a solid fat component. The emulsion component can comprise part of the ingredients that define a lipid component. In such aspects, the lipid component can be divided into emulsion lipids and non-emulsion lipids. In aspects, one or more fats are not contained in the emulsion.

Thus, in aspects, an emulsion is formed from certain components of the composition during the manufacture of NCs, which together can be considered an emulsion component and individually can be considered emulsion ingredients. In aspects, the emulsion component comprises most, materially all, essentially all, or all of the ingredients of the composition other than (a) the chocolate component, (b) the texturizing component, (c) the soluble fiber/psyllium component, and (d) cocoa butter. In aspects, at least 2 or more components or ingredients of the composition other that of (a)-(d) are mixed to form the emulsion component. In aspects, the emulsion component is added to the composition as a single ingredient. In some facets of the invention, this approach improves upon the manufacturing characteristics of the composition, e.g., composition viscosity characteristics, facilitating ease of manufacturing and reduced risk of clogging standard manufacturing equipment or problems with composition deposition over similar or equivalent compositions wherein ingredients of the emulsion are not pre-mixed but rather added individually to the composition. In aspects, the emulsion comprises at least one emulsifier, one or more lipid ingredients, and at least one starch. In aspects, the emulsion component aids in protecting the psyllium of the composition from significantly noticeable hydration (e.g., sufficient hydration capable of creating a negative organoleptic experience for the user during consumption, such as the creation of a slimy mouth feel) prior to the completion of mastication and swallowing.

According to certain embodiments, an emulsion component can comprise one or more lipid-rich ingredients (e.g., one or more of canola oil or coconut oil), one or more starches such as, e.g., cornstarch, one or more additives such as an extract, e.g., vanilla extract, and a lecithin, such as e.g., sunflower lecithin. In certain aspects, ingredients of the emulsion component are mixed separately and apart from any other ingredients of the nutritional composition. In aspects once mixed, such ingredients create the emulsion component which is then treated as a single ingredient and added as a single ingredient to other components of the nutritional composition. In aspects, the nutritional composition is a product formed by a manufacturing process whereby such an emulsion component is formed and added as a single ingredient to the remainder of the composition. In aspects, the psyllium of the composition is advantageously protected from hydration at a detectably higher level, e.g., by reducing the amount of hydration of the psyllium during manufacturing, storage, or while in use (e.g., during mastication and swallowing) by at least about 1%, at least about 3%, at least about 5%, at least about 10%, at least about 15%, or for example by at least 20%. than a similar composition made by a process not comprising such emulsion component formation and addition step. In aspects, the nutritional composition can be successfully manufactured using standard equipment in the art (e.g., specialized equipment designed for more highly viscous, sticky, or thick product) as opposed to similar compositions wherein such emulsion component formation and addition steps are absent. In aspects, formation of such an emulsion component and the addition of the emulsion component as a single ingredient measurably reduces manufacturing time and/or cost, reduces manufacturing down time due to equipment clogging or other types of equipment failure, measurably increases manufacturing unit production rates (e.g., number of individually packaged units which can be produced per given time period), or any combination thereof over similar compositions made without the formation and separate addition of such an emulsion component.

In aspects, an emulsion component makes up less than about 25 wt. % of an NC, such as less than about 22.5 wt. %, less than about 21 wt. %, or less than about 20 wt. %, such as less than about 18 wt. %, less than about 17.5 wt. %, less than about 15 wt. %, or less than about 12 wt. % of the NC. In aspects, the emulsion component makes up about 5 wt. %-20 wt. %, such as about 6 wt. %-18 wt. %, e.g., about 7 wt. %-about 14 wt. % of the total composition, e.g., about 5-15 wt. %, 4-14 wt. %, or 6-12 wt. %.

In aspects, the formation and use of an emulsion component (sometimes referred to as an emulsification component) can detectably or significantly prevent hydrophilic and hydrophobic ingredients from separating within the NC. The formation of an emulsion by some of the components in the manufacture of NCs also or alternatively can detectably or significantly aid in maintaining a suitable structure of chocolate, e.g., by detectably or significantly reducing or preventing the crystallization of chocolate ingredient(s). In aspects, an emulsion component of an NC also or alternatively detectably or significantly aids in preventing significant hydration of the fiber component within the composition (e.g., psyllium).

In yet another aspect, nutritional compositions can comprise an emulsifier, e.g., a single emulsifier ingredient or a combination of ingredients that make up an emulsification component. Emulsifiers typically can detectably or significantly promote the formation of an emulsion component (forming an emulsion faster, maintaining the emulsion longer or under more conditions, bringing more ingredients in contact with an emulsion into the emulsion, etc.). Emulsifiers that can provide such functions and are otherwise suitable for inclusion in NCs can include or comprise polysorbates, carrageenan, guar gum, mono- and di-glycerides, and one or more lecithin(s).

In aspects, NCs comprise an emulsifier ingredient/component, which detectably or significantly promotes the formation, maintenance, or other function/characteristic of the emulsion. The amount and nature of the emulsifiers and associated emulsion can detectably or significantly enhance the ability to economically manufacture NC at a largescale using food production equipment commonly used in production of products like NCs (e.g., one or more of depositors, blenders, cutters, conveyors, and the like), e.g., equipment used in mold production, deposition production, and the like (as contrasted to extrusion production).

In one aspect, one or more emulsifier ingredients or ingredients of an emulsification component can be any edible (e.g., safe for consumption) emulsifier capable of being incorporated into the composition and which further improve the manufacturing performance characteristics or the desired qualities of the final composition as they relate to consumer preference (for example, but not limited to, mouth-feel, taste, consistency, or, e.g., melted viscosity (as described further elsewhere herein)). Exemplary emulsifiers which can be incorporated include but are not limited to one or more of a lecithin (e.g., a soy, sunflower, or an egg lecithin), mucilage chemicals extracted from mustard, monoglycerides, diglycerides, diacetyl tartaric acid esters of monoglycerides or diglycerides, polysorbates, sodium phosphates, sodium stearoyl lactylate, carrageenan, guar gum, etc.

In one aspect, one or more lecithin(s) is/are used as an emulsifier, alone or in combination with other emulsifiers in an emulsifier component. An NC of the invention can comprise an emulsifier as a single ingredient (e.g., lecithin) and/or an emulsifier component (a mixture of two or more ingredients which together serve as an emulsifier for the composition), either or both of which can be present in an emulsification component, an emulsified component which in aspects is added to the composition as a single ingredient. Such an emulsification component may in aspects serve to further emulsify the composition. In aspects the emulsification component does not serve to further emulsify the composition. In another aspect of the invention, one or more lecithin(s) is/are contained in the NC, but is/are not added to the composition as a separate ingredient, and is not present in what is referred to here as the emulsion component. For example, in aspects lecithin is contained in the chocolate ingredient/component. In aspects, no lecithin is added to the NC beyond what is present in the chocolate component. In alternative aspects, lecithin is added as an emulsifier ingredient or added as a component of an emulsion component, hence added to or present in the NC by way other than as an ingredient of the chocolate component. In aspects, lecithin is provided in both the chocolate ingredient/component and in one or more other components, such as an emulsifier component, as an emulsifier ingredient, or as an element of an emulsification component.

A lecithin ingredient/component can be any suitable type of lecithin, including soy lecithin, sunflower lecithin, and egg lecithin.

In one aspect, the amount of lecithin in the composition outside of that contributed by the chocolate ingredient/component is less than about 1 wt. %, such as less than about 0.95 wt. %, less than about 0.9 wt. %, less than about 0.85 wt. %, less than about 0.8 wt. %, or less than about 0.75 wt. %. In an aspect of the invention, the total amount of lecithin added by ingredients other than the chocolate in the composition is less than about 0.25 wt. %, such as less than about 0.2 wt. %, less than about 0.175 wt. %, less than about 0.15 wt. %, less than about 0.125 wt. %, or less than about 0.1 wt. %. According to embodiments, the amount of lecithin in the composition added by ingredients other than the chocolate in the composition is between about 0.05 wt. % and 0.2 wt. %, such as between about 0.05 wt. % and 0.15 wt. %, such as between about 0.05 wt. %-0.175 wt. % or between about 0.05 wt. % and 0.1 wt. %. In certain embodiments, the amount of lecithin in the composition which is attributable to ingredients other than the chocolate ingredient(s) is between about 0.05 wt. % and 0.125 wt. %, between about 0.075 wt. % and 0.125 wt. %, or between about 0.075 wt. % and 0.1 wt. % of the composition.

In aspects, the emulsifier ingredient or component (to be clear, distinguishable from the emulsion or emulsification component); is at least in part a component of the emulsion component and makes up about 0.05 wt. %-5 wt. %, such as about 0.05 wt. %-about 3.5 wt. %, about 0.05 wt. %-about 2.5 wt. %, about 0.05 wt. %-about 1.5 wt. %, or about 0.05-about 1 wt. % of an NC. In certain embodiments, the composition comprises less than about 1 wt. % of any single emulsifier or, specifically, lecithin (outside of the chocolate component, totally, or both). For example, nutritional compositions can contain about 0.05-about 0.8 wt. %, about 0.05-about 0.75 wt. %, or about 0.05-about 0.7 wt. %, about 0.05-0.65 wt. %, about 0.05-about 0.6 wt. %, about 0.05-about 0.4 wt. % or about 0.05-about 0.3 wt. % lecithin outside of the chocolate component, in total, or both. In still other examples, nutritional compositions contain 0.065 wt. %-5 wt. %, about 0.065 wt. %-about 2 wt. %, about 0.065 wt. %-about 1.5 wt. %, about 0.065-about 1 wt. %, about 0.065-about 0.8 wt. %, about 0.065-about 0.75 wt. %, or about 0.065-about 0.7 wt. %, about 0.065-0.65 wt. %, about 0.065-about 0.6 wt. %, or about 0.065-about 0.5 wt. %, about 0.065-about 0.4 wt. %, or about 0.065-about 0.3 wt. % lecithin outside of the chocolate component, in total, or both. In still more particular aspects, the total amount of lecithin in the composition is less than about 5 wt. %, such as less than about 4.5 wt. %, less than about 4 wt. %, less than about 3.5 wt. %, less than about 3 wt. %, less than about 2.5 wt. %, less than about 2 wt. %, less than about 1.5 wt. % or less then about 1 wt. %, such as less than about 0.5 wt. % or even less. In aspects, the amount of lecithin in the composition is between about 0.075 wt. %-5 wt. %, such as about 0.075 wt. %-about 2 wt. %, about 0.065 wt. %-about 1.5 wt. %, about 0.075-about 1 wt. %, about 0.075-about 0.8 wt. %, about 0.075-about 0.75 wt. %, or about 0.075-about 0.7 wt. %, about 0.075-0.65 wt. %, about 0.075-about 0.6 wt. %, or about 0.075-about 0.5 wt. % or about 0.075-about 0.4 wt. % or about 0.075-about 0.3 wt. %; such as about 0.085 wt. %-5 wt. %, about 0.085 wt. %-about 2 wt. %, about 0.085%-about 1.5 wt. %, about 0.085-about 1 wt. %, about 0.085-about 0.8 wt. %, about 0.085-about 0.75 wt. %, or about 0.085-about 0.7 wt. %, about 0.085-0.65 wt. %, about 0.085-about 0.6 wt. %, or about 0.085-about 0.5 wt. %, about 0.085-about 0.4 wt. %, or about 0.085-about 0.3 wt. %; such as about 0.1 wt. %-5 wt. %, about 0.1 wt. %-about 2 wt. %, about 0.1 wt. %-about 1.5 wt. %, about 0.1-about 1 wt. %, about 0.1-about 0.8 wt. %, about 0.1-about 0.75 wt. %, or about 0.1-about 0.7 wt. %, about 0.1-0.65 wt. %, about 0.1-about 0.6 wt. %, or about 0.1-about 0.5 wt. %, about 0.1-about 0.4 wt. %, or about 0.1-about 0.3 wt. %; such as about 0.15 wt. %-5 wt. %, about 0.15 wt. %-about 2 wt. %, about 0.15 wt. %-about 1.5 wt. %, about 0.15-about 1 wt. %, about 0.15-about 0.8 wt. %, about 0.15-about 0.75 wt. %, or about 0.15-about 0.7 wt. %, about 0.15-0.65 wt. %, about 0.15-about 0.6 wt. %, or about 0.15-about 0.5 wt. %, about 0.15-about 0.4 wt. %, or about 0.15-about 0.3 wt. %; such as about 0.2 wt. %-5 wt. %, about 0.2 wt. %-about 2 wt. %, about 0.2 wt. %-about 1.5 wt. %, about 0.2-about 1 wt. %, about 0.2-about 0.8 wt. %, about 0.2-about 0.75 wt. %, or about 0.2-about 0.7 wt. %, about 0.2-0.65 wt. %, about 0.2-about 0.6 wt. %, or about 0.2-about 0.5 wt. %, about 0.2-0.4 wt. %, or about 0.2-0.3 wt. %.

According to embodiments, any lecithin contained in the composition is a non-GMO lecithin (according to other aspects, the composition is free of any GMO ingredients). According to embodiments, an NC is free of soy lecithin. According to aspects, an NC is free of any soy components, any peanut components, any gluten, or a combination of any or all thereof.

In aspects, compositions of the invention comprise at least about 5%, at least about 10%, at least about 15%, at least about 20%, at least about 25%, at least about 30%, at least about 35%, at least about 40%, at least about 45%, or at least about 50% less lecithin than the lecithin in the composition of the Erwin '134 application. In aspects, the nutritional composition described herein has, at the deposition step of the manufacturing process, a viscosity which is at least about 5% lower, at least about 10% lower, at least about 15% lower, at least about 20% lower, at least about 25% lower, at least about 30% lower, at least about 35% lower, at least about 40% lower, at least about 45% lower, at least about 50% lower or even more than that of the Erwin '134 composition during the same manufacturing step. In aspects, the nutritional compositions of the invention comprise at least about 10% less lecithin and exhibit at least a 20% lower viscosity at the deposition step of the manufacturing process than the compositions of the Erwin '134 application.

As used herein, the "deposition step" of the manufacturing process is defined as the step during which a mixture of ingredients (e.g., a composition) is placed, dropped, or allowed to fall from one location to another. Deposition in automated manufacturing processes is accomplished using a depositor, a piece of equipment specific for this purpose. In aspects, the nutritional compositions of the invention have a viscosity at the deposition step of the manufacturing process which allow for the composition to be deposited using industry standard deposition equipment (or allow for detectable or significantly better performance in using such equipment in terms of economic efficiency, loss of product, production time, etc.).

Other Additives

In one aspect of the invention, nutritional compositions can comprise, in addition to any of the ingredients or combinations of ingredients described elsewhere herein, one or more additives, used to maintain freshness or stability (e.g., extend shelf-life), preserve or enhance the flavoring, enhance the taste, texture, appearance, or coloring, or to enhance any other property of an NC. In other aspects, it can be desirable to exclude or limit certain other ingredients. Thus, compositions of the invention can be characterized based on inclusion of additional ingredients, exclusion of additional ingredients, or both.

In one aspect, NCs can comprise a thickening agent such as one or more starches, e.g. but not limited to cornstarch, carrageenan, gum(s) (e.g., but not limited to Arabic or xanthan gum), gelatin, or any similar thickener.

In another aspect, the composition can comprise a color additive such as FD&C Blue Nos. 1 and 2, FD&C Green No. 3, FD&C Red Nos. 3 and 40, FD&C Yellow Nos. 5 and 6, Orange B, Citrus Red No. 2, annatto extract, beta-carotene, grape skin extract, cochineal extract or carmine, paprika oleoresin, caramel color, fruit and vegetable juices, or saffron. In yet another aspect, the composition can comprise natural or artificial flavoring, or flavor enhancers such as Monosodium glutamate (MSG), hydrolyzed soy protein, autolyzed yeast extract, disodium guanylate or inosinate.

Nutritional compositions can further comprise pH control agents such as lactic acid, citric acid, ammonium hydroxide, or sodium carbonate. In another aspect, the composition can include any other food additive used to enhance any of the aforementioned or other properties of the composition such as salts, edible (safe for consumption) agents capable of serving as microbicides or preservatives, or other known additives. In some respects, NCs of the invention are free of preservative(s).

In still other aspects, the invention lacks any type of ingredient mentioned in any 1, 2, 3, 4 or all the preceding 4 paragraphs.

In another aspect of the invention, in certain embodiments, the nutritional composition also or alternatively does not contain any one or more of the following ingredients: inulin, almonds, xylose, sorbitol or other sugar alcohol(s), wheat dextrin, hydrolyzed starch, oligosaccharide, monosaccharide, disaccharide, polyglucose, polymaltose, maltodextrin, glycerin(e), peanut butter, humectants, leavening agent, ingredients characterized as "low glycemic," pectin, guar gum, senna, oat, pectin, chia seeds, fruit, supplements/vitamins, algae or seaweed, carrageenan, alginates, other algae-derived products, lactitol, cholestyramine, resistant or hydrolyzed starch, polyester, caffeic acid, chlorogenic acid, ferulic acid, xanthan gum, HPMC/HPC, arabinose, cyclodextrin, caramel, amino acids/protein (as separate/significant components), antibodies, corn fiber, wheat fiber, beta-glucan, probiotics/prebiotics, whole-grain product, polyethylene glycol (PEG), plasticizer, sterol/stanol-based component, or erythritol. According to another aspect, the amount of any one, combination, or all of any such ingredients makes up less than about 1.5 wt. % or 1 wt. %, such as less than about 0.5 wt. %, such as less than about 0.2 wt. %, less than about 0.1 wt. %, less than about 0.05 wt. %, or less than about 0.01 wt. % of the nutritional composition. In some aspects, a nutritional composition as described herein can comprise less than 1% trans-fat, such as less than 0.8% trans-fat, less than 0.6% trans-fat, less than 0.4% trans-fat, less than 0.2% trans-fat, or no trans-fat.

In some respects, the composition comprises, by means of their presence in one or more ingredients discussed herein or added as an additional ingredient, one or more ingredients providing nutritional value, such as one or more vitamins or minerals. In some respects, such an additional one or more nutrients adds to the nutritional value of the composition such that it contributes to the percent Daily Value (% DV) of such a nutrient.

For example, in some respects the composition comprises one or more of vitamin D, calcium, iron, or potassium. In some aspects, a serving of an NC described herein can comprise no vitamin D. In aspects, a serving of an NC described herein can comprise no calcium. In aspects, a serving of an NC described herein can comprise at least 1 mg of iron per serving, such as about 1.1 mg, about 1.2 mg, about 1.3 mg, about 1.4 mg, about 1.5 mg, or about 1.6 mg or about 1.7 mg of iron per serving. In aspects, such an amount can represent approximately 5% to about 10%, such as for example about 5%, about 6%, about 7%, about 8%, about 9%, or about 10% of the Daily Value (% DV) of iron. In some aspects, a serving of an NC described herein can comprise at least 60 mg of potassium, such as at least about 61 mg, about 62 mg, about 63 mg, about 65 mg, about 67 mg, about 69 mg, about 71 mg, about 73 mg, about 75 mg, or about 77 mg of potassium per serving. In some respects, such an amount can represent between approximately 1% and about 3% of the Daily Value of potassium, such as between about 1% and about 2% of the Daily Value (% DV) of potassium. In aspects, a serving of an NC described herein can comprise at least about 30 mg of calcium per serving, such as about 31 mg, about 32 mg, at least about 33 mg, at least about 34 mg, or at least about 35 mg of calcium per serving. In some respects, such an amount can represent between approximately 2% and approximately 4% of Daily Value, such as e.g., between approximately 2.5-3.5% daily value, e.g., about 3% DV of calcium.

Homogeneous Compositions

In some aspects of the invention, a nutritional composition can be characterized as a non-homogeneous blend of nutritional composition components. In alternative embodiments, a nutritional composition can be characterized as a homogeneous blend of nutritional composition components (a homogeneous composition).

In aspects, a nutritional composition is at least substantially homogeneous. As used herein, the terms "homogeneous" and "substantially homogeneous" both refer to a composition wherein at least about 65%, at least about 70%, or at least about 75%, such as at least about 80%, at least about 85%, at least about 90%, or at least about 95% (e.g., at least about 98%) of the nutritional composition differs from the average composition of the composition by no more than about 30%, such as by no more than about 25%, by no more than about 20%, or by no more than about 15%, such as by no more than about 10%, e.g., by no more than about 7.5%, or by no more than about 5%. For example, in an at least substantially homogeneous composition, at least about 60% of areas sampled of the composition (e.g., at least about 65%, at least about 70%, at least about 75%, or at least about 80% of the samples, at least about 85% of the samples, at least about 90% of the samples, or at least about 95% of the samples), taken from at least about 50% of the composition (e.g., at least about 60%, at least about 70%, at least about 80%, at least about 90%, or at least about 95% of the composition), will vary in terms of one or more compositional elements (e.g., texturizer component, total lipid, saturated lipid, or psyllium) by less than about 30%, such as less than about 25%, less than about 20%, or even less than about 15% from the average measurements of such one or more elements in the composition. However, in aspects, any other art-accepted definition of substantial homogeneity or homogeneity can alternatively be used in place of this definition to characterize compositions having such a uniformity of character as described. In some aspects, a homogeneous bar can be described as a bar wherein the bar does not comprise an area representing about 25% of the bar which differs from another area representing about 25% of a bar in content of an ingredient by more than 50%). In some aspects, a non-homogeneous bar can be described as a bar comprising at least one area representing about 25% of the bar which differs from another area representing about 25% of a bar in content of an ingredient by more than 50%. In aspects, no area of the NC in finished product form representing 25% of the NC varies in composition from the average composition of the NC by more than about 30%, by more than about 25%, by more than about 20%, by more than about 15%, by no more than about 10%, or for example by more than about 5%, such as by more than about 2%, or by more than about 1%. In aspects, an NC comprises no coating and wherein the compositional profile of any sampled area of the NC in finished product form representing 25% of the NC varies from the average compositional profile of the NC by more than about 20%, rendering the composition at least substantially homogeneous.

In one embodiment, at least about 75%, at least about 80%, at least about 85%, at least about 90% or more of the mixture is substantially homogeneous, such as at least about 92%, or at least about 94% of the mixture is characterizable as homogeneous, or for example, at least 96% or at least about 98% of the mixture is substantially homogeneous, or wherein between about 90-95%, between about 91-96%, between about 92-97%, between about 93-98%, or between about 94-99% of the mixture is homogeneous or substantially homogeneous.

Viscosity Characteristics

According to aspects, NCs can have a viscosity upon mastication (e.g., when melted or otherwise in liquified form in the mouth) which is approximately at least 1%, e.g., at least 2%, or for example at least 3% less than that of the compositions described in the AOS/Ervin '134 application, Metamucil® products, such as Metamucil® wafers, or both under certain conditions (e.g., in a ready to use state, during mastication, or both). In aspects, NCs have a viscosity that is least about 4% less than, at least about 6% less than, at least about 8% less than, or at least about 10% less than the average viscosity of the AOS/Ervin '134 application compositions or Metamucil® products, such as Metamucil® wafer products, or both, in one or more conditions.

In one aspect of the invention, the compositions of the invention provide for a lower frequency of choking, gagging, or similar experience than that experienced by the consumers upon the ingestion of other fiber-containing products as measured by an appropriately controlled study or consumer survey. According to certain embodiments, the rate of choking is reduced by, e.g., about 5%, about 10%, about 15%, about 20%, about 25%, about 30%, about 35%, about 40% or more over other fiber-containing food products intended to provided supplemental dietary fiber, such as Metamucil® products (e.g., Metamucil® wafers) or products produced according to the Ervin '134 application, as measured by an appropriately conducted trial or survey.

Coated/Uncoated Compositions

As used herein, a "coating" can be any kind of edible (safe to consume) coating suitable for creating a coated layer on at least one side of the composition (for example, a coating could be a layer added only to the top, only the bottom, or for example only to one end or a coating could be applied to the entire final formulation). Such a coating can be a soft coating or a hard coating (e.g., a crunchy coating). In aspects a coating detectably modifies (e.g., enhances) the textural characteristics of a final product. In aspects, the coating can comprise, predominately comprise, or be a chocolate (such as, for example, a white chocolate coating over a milk or dark chocolate-comprising composition). In alternative aspects, a coating imparts a different flavoring than the main body of the final product (e.g., the composition(s) described herein), such as for example the coating could comprise other flavors such as vanilla, strawberry, peanut butter, fruit, caramel, yogurt, and the like. In some aspects, the coating itself could comprise one or more additional flavor or textural elements such as nuts, crisps, cookie pieces, berries or fruits, candy pieces, or any other similar or equivalent elements which may appeal to a wide range of consumers.

Nutritional compositions described herein can be uncoated or coated. In one aspect, NCs lack any additional coating; that is, there is no additional outer layer added to any one or more surfaces of the composition to cover or encapsulate the composition(s). For example, nutritional compositions can be characterized in lacking any glaze, icing, or coating layer, such as an additional chocolate coating layer.

In one embodiment, nutritional compositions can be in a final product form, for example, in the form of a single-serving or partial serving-sized bar. In aspects, such a bar can be uncoated, partially, or entirely coated.

Composition/Bar Physical Characteristics

In one embodiment, the present composition can be in the form of a single-serving formulation having a non-extruded base or body. In one aspect, the composition is or is at least substantially homogeneous (or essentially homogeneous or homogeneous) base or "body." E.g., in aspects the composition can be in the form of a single-serving formulation such as a bar wherein the base or body of the bar does not comprise an area representing about 25% of the bar which differs from another area representing about 25% of a bar in content of an ingredient by more than 50%. In aspects, the formulation can be in the form of a consumable bar which can, in certain aspects, be uncoated, partially coated, or entirely coated. According to embodiments, an NC is in the form of a consumable bar which is uncoated.

Nutritional compositions can deliver a beneficial amount of dietary fiber to a consumer with significant reduction in undesirable mouthfeel ("slimy," "sticky," or "film-like," sensation(s)) and other negative properties associated with on-market and prior art psyllium-containing fiber products.

Serving Sizes

Nutritional compositions can be sized appropriately for a partial, a single, or more than one serving size(s) as part of a regular diet. Such a finished consumable (unit) product comprising, predominately comprising, materially comprising, essentially comprising, or consisting of an NC, can be in any suitable form, e.g., in snack shapes, wafers, cookies, or a snack/food bar.

In some embodiments, such a finished product can be in the form of a food bar, e.g., in the form of a chocolate-based bar. Such a food bar could have any size or shape suitable for consumption by a consumer. In a further aspect the finished product can be in a form such that the nutritional composition in finished product form can be in the amount of, e.g., have a serving size of about 10 g to about 100 g, such as for example about 12 g to about 96 g, such as for example about 12 g, about 15 g, about 20 g, about 25 g, or about 30 g, such as for example about 35 g, about 40 g, about 45 g, or about 50 g, as in about 55 g, about 60 g, about 65 g, about 70 g, about 75 g, about 80 g, about 85 g, about 90 g, about 95 g, about 97 g, or about 99 g, as in for example a serving size of between about 10-80 g, between about 10-70 g, between about 10-60 g, between about 10-50 g, between about 10-40 g, or between about 10-30 g, as in between about 15-95 g, between about 15 g-80 g, between about 15-65 g, between about 15-40 g, or for example between about 20 g and about 40 g or have a serving size of between about 20 g and 30 g. Alternatively, suitable serving sizes are provided and exemplified elsewhere herein. In aspects, a single serving size is approximately 24 g.

In another aspect, a 10-100 g composition can comprise multiple servings, for example, such a 10-100 g bar could represent a serving size of about ½ to about four servings of the composition, such as about a half of a serving, such as a single (1) serving, such as about two servings, such as about three servings. In another aspect, the present composition can be consumed to suppress appetite or to facilitate a reduction of total caloric intake throughout a 24-hour period. Exemplary times for consumption for such purpose(s) can be before, or with at least one meal, such as for example about 2 hours before a meal, about 1 hour before a meal, such as 45 minutes before a meal, such as 30 minutes before a meal, such as 15 minutes before a meal, or, e.g., concurrently with a meal.

In one aspect, a single-serving product comprises a serving size of about 24-30 g, for example, about 24 g, or about 25 g, or about 26 g, or about 27 g, or about 28 g, or about 29 g, or about 30 g. In aspects, a single-serving product is a single serving finished product to be consumed once per day. In alternative aspects, a single-serving product is a single-serving finished product wherein more than one sub-serving is consumed per day.

In other aspects, a finished NC product can be divided into sub-servings, such as, for example, portions of about 2 g, or about 3 g, or about 4 g, or about 5 g, or about 6 g, or about 10 g, or about 15 g that can be taken one or more times per day, such as for example, as may be exemplified by the composition being available in bite-sized portions.

In some aspects, an NC product can comprise at least 10 g of chocolate per 24 g serving size of finished product, such as for example at least about 10 g, at least about 11 g, at least about 12 g, at least about 13 g, at least about 14 g, at least about 15 g, at least about 16 g, at least about 17 g, or at least 18 g of chocolate per 24 g serving; such an amount may be adjusted such that the same ratio of amount chocolate per serving to total serving size is maintained if the serving size varies from 24 g.

In some aspects, the NC product can comprise less than about 150 calories per serving, such as for example less than about 140 calories per serving, less than about 130 calories per serving, or less than about 120 calories per serving, such as about 110 calories per 24 g serving. In aspects, a single unit can represent a fraction of a serving size (e.g., 1/2 serving). In such aspects, a single unit can provide between approximately 15-90 calories, such as between about 20-85 calories, between about 25-80 calories, between about 25-80 calories, between about 30-75 calories, or for example between about 35-70 calories. In certain aspects, the total calories consumed per day from servings/units of NC can be between, e.g., about 20-440 calories, such as for example between about 20-420 calories, between about 20-400 calories, between about 20-380 calories, between about 20-360 calories per day, such as, for example, between about 30-360 calories, between about 40-340 calories, or for example between about 50-330 calories per day, such as, for example, between about 55-330 calories per day from the composition(s).

Manufacturing

Nutritional compositions can be produced by any suitable means. Techniques for predominately homogenously, substantially homogeneously, homogenously, or otherwise mixing ingredients/components such as lipid(s)/lipid-rich ingredients, chocolate, psyllium, an emulsion component (if present), and, if present, texturizing element(s), are known in the art. Techniques are known for producing nutritional compositions having the characteristics described here, including forming at least predominately, substantially, or homogeneously blended compositions through the blending/mixing of ingredients.

In one aspect, the composition is produced by a method that excludes any step that requires extrusion of the product.

In one aspect, the composition also or alternatively is not baked at high temperatures (e.g., above 300, above 350, or above 400 degrees F.) for a substantial period of time (e.g., more than about 20 minutes, more than about 30 minutes, more than about 40 minutes, or more than about 1 hour). In one aspect, the NCs are not baked at all.

In one aspect, the method comprises the use of an emulsion of two or more of the ingredients in the production of the NC (as also discussed above). In aspects, the method comprises the creation of an emulsion component, the emulsion component then added as a single ingredient during the manufacturing process. In aspects, the emulsion component comprises two or more ingredients. In aspects, the emulsion component comprises at least one emulsifier ingredient. In aspects, an emulsifier ingredient can be added as a single ingredient during manufacturing. According to embodiments, in at least one phase of the manufacturing process, at least about two of the ingredients in the composition, together with an emulsifier are emulsified, then further combined with other ingredients in the formulation including the psyllium, resulting in a composition within which the psyllium is detectably or significantly surrounded and protected from contact with water. In aspects, the psyllium or fiber component does not absorb more than 20% of the fiber's/psyllium's water holding capacity during manufacturing, storage, or in use (e.g., during mastication).

In aspects, the emulsification component, the addition of the emulsification component as a single ingredient during manufacturing, or both prevent NCs from detectably or significantly thickening (increasing in viscosity) during manufacturing resulting in detectable or significant amounts of machine or line clogging; nutritional composition clumping or sticking; or the fiber component otherwise impeding a manufacturing process (e.g., impeding successful deposition), particularly at larger, commercially relevant scale ("at scale"). The term "at scale" in this respect can mean production of a batch of NC material of at least about 100 pounds, at least about 200 pounds (lbs), at least about 500 lbs, 1000 lbs, or at least about 2000 lbs.

In aspects, similar compositions manufactured without the emulsion method, or e.g., having a higher lecithin content, lower saturated lipid content, or combination thereof can result in an increase of cost, loss of product yield, or delay of manufacture of at least about 5%, at least about 10% at least about 15%, at least about 20%, or at least about 25% as compared to production of the present composition.

The manufacture of NCs can comprise use of conventional manufacturing methods, such as kettle, tank (e.g., swept tank), or vessel mixing/blending. Components/ingredients can be loaded into mixing vessels from hoppers or other containers. In aspects, materials are transported via conveyer to different parts of a manufacturing process, such as mixers, shapers/cutters, and the like. Filters and components for removing fines and the like, dividers, de-lumpers, and other conventional components for modifying the physical characteristics of NC products can be incorporated into the manufacturing process.

In some aspects, the invention is a psyllium-containing nutritional composition which can be useful in the management of dietary fiber-related health matter such as, for example, appetite or regularity, which can be made by a process comprising addition of an emulsion component as a single ingredient. In aspects, NCs described herein can be made by a process comprising establishing an emulsion comprising one or more components, such one or more components comprising, primarily comprising, materially comprising, or at least essentially comprising, consisting essentially of, or consisting of a coconut oil, a vegetable oil, a starch, and an emulsifier. In certain embodiments, such an emulsion component can comprise coconut oil in an amount representing about 0.8-0.95 wt. % (e.g., 0.83-0.91 wt. %, such as about 0.87 wt. %) of the composition. In certain aspects, such an emulsion component can comprise a vegetable oil in an amount representing between about 1.5-2.3 wt. % of the composition (e.g., 1.7-2.1 wt. %, such as about 1.9 wt. %). In aspects, such a vegetable oil can at least primarily be comprised of canola oil. In aspects, such an emulsion component can comprise a starch in an amount representing between about 3-6 wt. % of the composition. In aspects, the starch can be at least primarily comprised of a corn starch. In aspects, such an emulsion component can comprise an emulsifier in an amount representing between about 0.075-0.125 wt. % of the composition (e.g., about 0.1 wt. % of the composition). In aspects such an emulsifier can be a lecithin, such as a soy or a sunflower lecithin.

According to some aspects, the process of making compositions described herein can further comprise blending the emulsion as an ingredient (e.g., as a single ingredient) with other ingredients of the composition, such as, e.g., psyllium, a chocolate component, a non-emulsion lipid component separate from the chocolate component, and a texturizing element. In aspects, the emulsion can be blended with psyllium, in an amount representing between about 10-18.5 wt. % of the NC. In aspects, the emulsion can be blended with a chocolate component in an amount representing between about 55-67.5 wt. % of the NC. In aspects, the emulsion can be blended with a non-emulsion lipid component separate from the chocolate component in an amount representing between about 5-10 wt. % of the total composition. In aspects, a non-emulsion lipid component is a lipid ingredient or component which is separate from the chocolate and which is not a part of the emulsion component. In aspects, such a non-emulsion lipid component can be cocoa butter. In aspects, the emulsion can be blended with a non-psyllium texturizing element in an amount representing between about 5-15 wt. % of the total composition. In aspects, such a non-psyllium texturizing element can be a crisp rice.

In aspects, the process described in the preceding two paragraphs can yield a composition comprising between about 16 wt. %-about 20 wt. % of a saturated lipid, between about 11-15 wt. % unsaturated lipid, at least about 28%, such as at least about 29%, at least about 30%, at least about 31%, or at least about 32% total lipids, or any or all thereof. In aspects, the process can yield a composition wherein the ratio of lipids contributed by the chocolate component to the lipids contributed by the combination of lipids of the emulsion component and the non-emulsion lipid component is between 1.25:1-2.75:1. In certain aspects, the process does not comprise an extrusion step, e.g., the composition is made into final form using a manufacturing step other than extrusion, e.g., utilizes a deposition step or is made via molding.

Packaging and Packaged Products

In another aspect, the nutritional compositions described herein can be provided in a finished product form, such a finished product being in a packaged or wrapped form. The packaging can be any packaging suitable for maintaining the integrity of the product, such as packaging that prolongs shelf life and protects the product from contamination. In aspects, packaging can be individually wrapped, single-serving packages. In aspects, packaging can be multiple serving packages, or, for example, daily serving packages. According to embodiments, packaging is capable of detectably promoting/maintaining shelf life or preventing contamination of the compositions until opened.

In some aspects, packaging can be a plastic, foil, paper, a waxed paper or foil, or any similar or equivalent packaging or combination of any such types of packaging and can incorporate one or more seals, zippers, closures, or compartments to further assist with preventing contamination of the compositions. In aspects, packaging can detectably or significantly protect the product from air (isolate the product from contact with the environment). In aspects, packaging is at least materially airtight. In other aspects, packaging is not airtight. In some respects, the packaging may be resealable. Packaging may further comprise elements to aid the consumer in opening the packaging, such as notches, tabs, or other similar aids known in the art to aid a wide range of consumers, including older consumers, in accessing the product.

In certain aspects, packages of two or more of such individually wrapped serving-size or partial serving-size products (e.g., product units) are provided. Such packages can contain at least 2, at least 3, at least 4, at least 5, at least 6, at least 7, at least 8, at least 10, at least 12, at least 14, at least 15, at least 20, at least 21, at least 24, or at least 30 individually wrapped servings (e.g., 2-31 servings, 2-30 servings, 2-28 servings, 2-24 servings, 3-24 servings, 3-21 servings, 3-12 servings, 3-9 servings, 4-12 servings, or 4-8 servings). In aspects such packages can be designed to provide the consumer with, e.g., 1-week or e.g., 1-month supply of product. In specific aspects, packages can comprise individually wrapped units of product wherein one or more individually wrapped units represent a single serving. Such packages can comprise any number of individually wrapped product units to attain any number of individual servings. For example, in specific aspects, individually wrapped units of product can each be ½ of a serving size (e.g., 2 individually wrapped product units represent 1 serving), and, for example, 10, 12, 16, 20, 24, or e.g., 48 individually wrapped units can be packaged together such that the packaging comprises 5 single servings, 6 single servings, 8 single servings, 10 single servings, 12 single servings, or e.g., 24 single servings.

Stability and Shelf Life

In another aspect of the invention, a finished product of the invention can be characterized as "shelf-stable." Shelf stability reflects compositions packaged in finished product form.

Shelf-stable NC products are capable of withstanding prolonged storage without refrigeration without significant occurrence (e.g., less than about 5%, less than about 2%, or less than about 1%) of a significant amount of degradation of the product (e.g., in terms of product loss, bacterial contamination, deformation of the product), typically on average (as determined by testing numerous products), over a period of storage under typical environmental temperatures (e.g., about 5-26 degrees C.) or near-room-temperature conditions (e.g., about 10-about 25 degrees C.). Such products may be shelf-stable in low humidity environments or at specific temperatures, such as near-room-temperature temperatures or room temperature. In one aspect, compositions of the invention in finished product form are stored in a location with relative humidity not exceeding about 60%. In another aspect, the compositions of the invention in finished product form are capable of maintaining shelf-stability when stored between about 10-about 26° C., such as for example at about 10° C., about 12° C. about 16° C., about 18° C., about 23° C., about 24° C., about 25° C., or at about 26° C., such as for example between about 10-26° C., between about 10-24° C., between about 12-26° C., between about 12-24° C. or between about 14-26° C., as in for example between about 14-24° C., or between about 18-26° C., such as for example between about 20-26° C. According to certain aspects, the compositions of the invention are capable of maintaining shelf-stability when stored at a temperature ranging from between 10-26° C. of between about 1-2 years, such as for example between about 12 months and about 24 months, between about 12 months and about 20 months, or between about 12 months and about 16 months, such as for example between about 16 months and about 24 months, or between about 20 months and 24 months.

Methods of Diet/Health Maintenance//Consumption of Products

Compositions of the invention can be consumed as part of a dietary regimen over a defined or indefinite period of time, either as an occasionally consumed food item or regularly consumed item, which may be used for supporting, promoting, or accomplishing a health result, such as those known in the art to be associated with consumption of psyllium products (e.g., maintenance of regular bowel movements), examples of which are described in the Background of this disclosure.

Escalating Dose

In aspects, the invention is a method of supplementing the amount of dietary fiber in a person's diet, wherein the amount of composition recommended for consumption per day for a first time period (e.g., a first week) of supplementation can be equal to or lower than the amount of composition recommended for consumption per day for a period following the first period (e.g., weeks following week one). In some aspects, the invention is a method of supplementing the amount of dietary fiber in a person's diet using an escalating dose schedule, whereby the amount of composition consumed per day starting in a second time period (e.g., week 2) of supplementation is greater than the amount of composition consumed per day in a first time period (e.g., week 1).

In aspects, the invention provides a method of supplementing the amount of dietary fiber in a person's diet comprising administering to the person 1 unit of a psyllium-containing nutritional composition per day with about 8 ounces of water for a first period, such as for example 1-7 days, e.g., about 1 week, wherein the unit represents e.g., a fraction of a single serving size or a serving size. In some respects, a unit can comprise more than one serving. In aspects, the method can comprise increasing the amount of composition after the first period, e.g., starting in week 2 (day 8) of supplementation, such as increasing consumption to more than one unit, such as at least one unit, at least 2 units, at least 3 units, at least 4 units, at least 5 units, or for example 6 units. In aspects a composition may be consumed one to three times per day. In some aspects at least 8 oz of water, such as at least 8 oz, at least 9 oz, at least 10 oz, at least 11 oz, at least 12 oz, at least 13 oz, at least 14 oz, at least 15 oz, or for example at least 16 oz is consumed each time a psyllium-containing composition is consumed.

Consumption with Water

In aspects, the minimum suggested amount of water to be consumed with a serving of NC is detectably or significantly reduced as compared to currently sold psyllium products, e.g., Metamucil® wafer products.

In an aspect of the invention, a safe and effective amount of fiber supplement can be delivered to a consumer by administering the co-consumption/combination of water and composition in a ratio of about 1 g composition:at least about 0.22 ounce (oz) of water or more, such as about 1 g composition:at least about 0.4 oz of water, about 1 g composition:at least about 0.6 oz of water, about 1 g composition:at least about 0.8 oz of water, about 1 g composition:at least about 1 oz of water, about 1 g composition:at least about 1.2 oz water, about 1 g composition:at least about 1.4 oz water, about 1 g composition:at least about 1.6 oz of water, about 1 g composition:at least about 1.8 oz of water, or about 1 g composition—at least about 2 oz water or more, (e.g., at least about 5 oz water for each 24 g serving of composition consumed in a period, such as in one day or less).

According to certain aspects, the amount of recommended water consumed with the product can vary depending on how long a consumer has been consuming the product, as the consumer, or any personnel guiding their consumption of the product as discussed elsewhere herein, will become familiar with how the consumer's body reacts to the consumption of the product, e.g., how ingestion is tolerated (e.g., choking tolerance) or how weight or regularity are affected. In certain embodiments, the recommended ratio of serving size to water consumption is higher when first consuming the product and lower after the consumer has been consuming the product for a given period, such as daily for at least one week. Also or alternatively, the ratio of serving size to water consumption is higher (e.g., more composition can be consumed with less water) once the consumer or anyone potentially guiding their consumption has become familiar with or accustomed to the product or knows how the consumer's body will digestively react to the consumption of the composition. In an alternative aspect, the composition can be ingested by the consumer without requiring consumption with water. For example, in one embodiment the minimum amount of water is reduced from 1 oz per every 1.5 g composition consumed to 1 oz water per every about 1-4.5 g of composition, every 1-3.5 g of composition, or every 1-3 g of composition (such as about 16 or 48 oz of water consumed for every about 24-72 g of composition, or e.g., reduced from 16 oz of water consumed with each 24 g bar (alternatively stated, from 8 oz of water consumed with each 12 g bar) to 16 oz of water consumed with each 1-3 bars (24-72 g composition).

According to another aspect, the consumption of the nutritional product also or alternatively requires consuming less than about 8 oz of water per each about 5 g of psyllium.

In still another facet, the nutritional product is administered over a period of time and ratio of ounces per water to grams of composition consumed per day in at least part of the period is also or alternatively less than 1, such as at less than about 0.8, less than about 0.75, or less than about 0.7, such as in a ratio of between about 0.1-1, about 0.1-0.9, or about 0.1-0.8.

In aspects, because hydration of psyllium is preferred once mastication and swallowing is complete (so as to avoid gelling and swelling whereby the consumer has a negative organoleptic experience such as a slimy feel in the mouth, yet provide the "flushing" effect of hydrated psyllium in the gastrointestinal tract to support, e.g., bowel movement regularity), consumption of the NCs of the present invention may beneficial, such as for example consumption of at least 8 oz of water per serving (e.g., per 24 g of nutritional composition).

Appetite Suppression

Another aspect of the invention comprises a method of inducing appetite suppression or reducing daily caloric intake, by administering between 10 g and 100 g, such as between about 12 g and 96 g (such as, for example, approximately 12 g, approximately 24 g, approximately 36 g, approximately 48 g, approximately 60 g, approximately 72 g, approximately 84 g, or approximately 96 g) of the composition for a set period of time, such a period of time being for example about five days, about ten days, about 15 days, about 20 days, about 25 days, or about 30 days, such as for example between about 7-14 days, between about 14-21 days, between about 21-28 days, as in for example between approximately 7-21 days, or for example between approximately 14-28 days, wherein the caloric intake of the consumer is monitored over the set period of time, and wherein the amount of nutritional composition is adjusted up or down according to a targeted daily caloric intake goal of the consumer. In some aspects, if a consumer responds to the consumption of the composition in such a way that appetite suppression is too high and overall caloric consumption is too low, e.g., leading to sub-optimally fast weight loss, consumption may be decreased or increased accordingly. Also or alternatively, if a consumer responds to the consumption of the composition in such a way that appetite suppression is too low, e.g., leading to no weight loss or weight gain, consumption may be decreased or increased accordingly.

In a related aspect, the method can be repeated 2 or more times, such as for example about 2 more times, about 3 more times, about 4 more times, about 5 more times, or more, such as about 6 more times, about 7 more times, about 8 more times, about 9 more times, or about 10 more times or more until an optimal daily amount of nutritional composition is established that meets the targeted daily caloric intake goals of the consumer, and wherein, upon establishing the optimal amount of nutritional composition to be consumed daily, the consumer continues to consume the established amount of nutritional composition daily to maintain the targeted caloric intake. In aspects, such amounts or repetitions of administration can be established and adjusted according to the tolerance of the individual, e.g., to a level whereby the individual does not experience intolerable or undesirable discomfort or pain.

In an aspect of the invention, the composition can be administered as part of a professionally monitored diet plan, e.g., a diet plan administered by, guided by, or otherwise facilitated by a trained individual such as a physician, dietitian, or other trained healthcare professional. Such a diet plan could be used to guide the consumption of the compositions described herein for any individual consumer or group of consumers; however, such a plan may find particular utility in guiding individuals having a proclivity for, craving, or affinity for sweet, non-nutritious snacks or food products. Individuals having a preference for sweet food products may be more willing to consume the composition presented herein as opposed to dietary fiber supplementation products in the forms of powders, pills/tablets, or wafers, especially if recommended multiple times per day. In a further aspect, the composition can be administered as part of a self-controlled diet plan. In aspects, such plans can be established and adjusted according to the tolerance of the individual, e.g., to a level whereby the individual does not experience intolerable or undesirable discomfort or pain.

Regularity Control

In an aspect of the invention, a nutritional composition can be administered as part of a method for maintaining digestive regularity. As used herein, digestive regularity refers to a somewhat established pattern or a number of bowel movements in a given period of time, such as for example typically ranging from about three bowel movements per day to three bowel movements per week depending on an individual's diet, age, and level of activity. According to certain aspects, a nutritional composition can be administered in an amount ranging between about 10 g and 100 g daily for a set period, during which time the digestive regularity of the individual is monitored, and wherein the amount of nutritional composition is adjusted up or down according to a targeted daily regularity goal of the individual. For example, in certain aspects, an individual can consume between about 10 g and about 100 g of a composition of the invention per day and if the number of bowel movements within an established period is not sufficient to reach a preferred, optimum, or otherwise sufficient rate to maintain optimal digestive health, or alternatively if the number of bowel movements within an established period is too high to cause inconvenience, discomfort, or otherwise not supportive of optimal digestive health, the amount of composition consumed per day can be increased or decreased accordingly.

In a related aspect, the method can be repeated 2 or more times, such as for example about 2 times, about 3 times, about 4 times, about 5 times, about 6 times, about 7 times, about 8 times, about 9 times, or about 10 times or even more until an optimal daily amount of nutritional composition is established that meets the targeted regularity goal of the individual or guiding professional, and wherein, upon establishing the optimal amount of nutritional composition to be consumed daily, the individual continues to consume the established amount of nutritional composition daily to maintain the targeted regularity goal. In aspects, consumption levels can be established and adjusted according to the tolerance of the individual, e.g., to a level whereby the individual does not experience intolerable or undesirable discomfort or pain. In embodiments, the amount of consumers that exhibit a preference for the product when consumed or when consumed regularly for a period, such as a period of at least about 1 week, at least about 2 weeks, at least about 1 month, at least about 3 months, that prefer the composition of the invention is at least about 10% greater, at least about 15% greater, or at least about 25% greater than those that prefer Metamucil® products, such as Metamucil® wafers. In some embodiments, consumption of the product over any such period of time is associated with an at least about 3%, at least about 5%, at least about 10%, at least about 15%, or at least about 20% reduction in adverse events, such as choking, gagging, etc., associated with consumption of a comparator psyllium product, such as currently marketed Metamucil® products.

Mouthfeel & Consumer Preference

In an aspect of the invention, the disclosed compositions provide for a lower consumer-reported negative mouthfeel, or feeling of a film-coating left in mouth/throat after consumption, such as at least about 5% lower, at least 10% lower, at least about 15% lower, at least about 20% lower, at least about 25% lower, occurrence or severity of such experiences (e.g., as measured on a 5-point, 3-point, 7-point, 10-point, 20-point, or 100 point scale) as compared to one or more comparator prior art psyllium compositions, such as one or more currently-marketed Metamucil® products, compositions of the Ervin/AOS '134 application, or both.

In another aspect of the invention, the disclosed compositions also or alternatively provide for less frequent consumer-reported choking, or gagging, or coughing during consumption such as at least about 3%, at least about 5%, at least about 7.5%, at least about 10%, at least about 12%, or at least about 15% reduction in adverse events in a population of consumers using the product, such as choking, as compared to such one or more prior art psyllium products, such as products of the '134 application or current Metamucil® products, such as Metamucil® wafers.

In yet another aspect, nutritional compositions provide for a better consumer-reported preference in taste, texture, mouthfeel, overall experience/enjoyability, perceived moistness (lack of dryness), or any combination thereof, or in likelihood of continued/repeated use, such as in at least about 5%, at least about 7.5%, at least about 10%, at least about 12%, at least about 15%, or at least about 20% of consumers, as compared to both the earlier-attempted AOS '134 application products and currently-marketed Metamucil® products.

In another aspect, nutritional compositions provide for an increased overall consumer-reported willingness to continue ingestion of the inventive compositions, such as at least about 5% more, at least about 10% more, at least about 15% more, or at least about 20% more of consumers are willing to continue use of the inventive product composition over the currently-marketed Metamucil® products or a composition of the '134 Ervin application.

EXPERIMENTAL DATA

The following experimental data (Example) is provided to illustrate certain aspects of the invention, without limiting its scope.

A hydration test was performed to evaluate the extent to which the fiber element of a nutritional composition of the invention absorbed water over time and to establish the extent to which the structure of the finished product is maintainable when fully immersed in an aqueous environment. The fiber hydration test was performed using two formulations of nutritional compositions in conjunction with four comparator products. Comparator products were selected based on their intended use and market popularity as fiber supplementation products.

Two nutritional composition products with different formulations/ingredients were manufactured according to Table 1 (below) and made into finished form, 12 g fiber-rich chocolate bars. The method of manufacturing comprised the creation of an emulsion component as described elsewhere herein, the emulsion component added as a single ingredient during the manufacturing process.

TABLE 1

| Milk Chocolate Composition (12 g serving) Ingredient | Dark Chocolate Composition (12 g serving) Ingredient |
| --- | --- |
| Milk Chocolate (comprising Sugar, Cocoa Butter, Whole Milk Powder, Unsweetened Chocolate, Nonfat Dry Milk, Milkfat, Soy Lecithin, Vanilla Extract) | Dark Chocolate (comprising Sugar, Unsweetened Chocolate, Cocoa Butter, Unsweetened Chocolate Processed with Alkali, Milkfat, Soy Lecithin, Vanilla Extract) |
| Psyllium Seed Husk | Psyllium |
| Rice Crisps (comprising Rice Flour, Sugar, Barley Malt Extract, Salt, Distilled Monoglycerides, Partially Hydrogenated Vegetable Oils [Cottonseed and Soybean Oil], Rice Extract) | Rice Crisps (comprising Rice Flour, Sugar, Barley Malt Extract, Salt, Distilled Monoglycerides, Partially Hydrogenated Vegetable Oils [Cottonseed and Soybean Oil], Rice Extract) |
| Cocoa Butter | Cocoa Butter |
| Cornstarch | Cornstarch |
| Canola Oil | Canola Oil |
| Virgin Coconut Oil | Coconut Oil |
| Vanilla Extract | Vanilla Extract |
| Sunflower Lecithin | Sunflower Lecithin |

Competitor products used in the study are shown in Table 2, below.

TABLE 2

| Product | Manufacturer |
| --- | --- |
| Meta Apple Crisp Fiber Thins (2 wafers/1 serving) Meta Chocolate Fiber Thins (2 wafers/1 serving) Meta Cinnamon Fiber Thins (2 wafers/1 serving) Metamucil Sugar-Free Orange Smooth Powder (1 rounded teaspoon (1 serving; 3.4 g psyllium) in 8 ounces of water) | Procter & Gamble |

A single milk chocolate fiber bar of the invention, a single dark chocolate fiber bar of the invention, and a sample of each of the competitor products were placed in individual cups of water at room temperature. All products were completely submerged.

Observations of the product structure were made at 5 minutes, 10 minutes, 15 minutes, 25 minutes, 30 minutes, and 45 minutes post-submersion. A separate, thin wooden stirrer having the dimensions 7 inches long by 0.25 inches wide was used to gently move the products in the glass of water to obtain an accurate read on deterioration at each time point.

The observations described above were recorded in Table 3, below.

TABLE 3

PRODUCT STRUCTURE - OBSERVATIONS

| TIME (min) | Milk Chocolate Comp. | Dark Chocolate Comp. | Meta Apple Crisp Fiber Thins | Meta Chocolate Fiber Thins | Meta Cinnamon Fiber Thins | Metamucil Powder |
|---|---|---|---|---|---|---|
| 5 | Little to no compromise/ deterioration. | Little to no compromise/ deterioration. | Outer layer starting to deteriorate; small flakes from wafers were starting to fall off the outer layer. | Significant water absorption; wafers breaking in half and clearly swelling. | Outer layer starting to deteriorate; small flakes from wafers were starting to fall off the outer layer. | Consistency changed slightly, starting to become gel-like. |
| 10 | Little to no compromise/ deterioration. The very outer layer (chocolate only) starting to deteriorate but the only very surface of the bar. | Little to no compromise/ deterioration. The very outer layer (chocolate only) starting to deteriorate but the only very surface of the bar. | Wafers were swelling and breaking down further, still in one piece. | Wafers have fallen apart and are just small chunks that break apart at the slightest touch. | Wafers are swelling and breaking down further, still in one piece. | Consistency getting thicker; more gel-like. |
| 15 | No change in deterioration status from the 10-minute time point. | No change in deterioration status from the 10-minute time point. | Wafers starting to break apart slightly; small pieces falling off edges; swelling increased. | Wafers completely deteriorated, only full of flakes. | Wafers starting to break apart slightly; small pieces falling off edges; swelling increased. | Thicker consistency, noticeable when stirring. |
| 25 | No change in deterioration status from the 15-minute time point. | No change in deterioration status from the 15-minute time point. | Wafers have broken apart and are in large chunks. | Completely deteriorated, just a glass full of sediment remaining. | Wafers have broken in half and are deteriorating quickly. | Even thicker consistency, the wooden stirrer can almost be held upright in the glass without any support. |
| 30 | No change in deterioration status from the 25-minute time point. | No change in deterioration status from the 25-minute time point. | Wafers have heavily deteriorated; chunks left along with sediment. | Completely deteriorated, water full of sediment is starting to become slightly gel-like. | Wafers have almost completely deteriorated; only small chunks left floating around along with sediment. | Even more gel-like, the wooden stirrer can stand straight up in glass without any support. |
| 45 | No change in deterioration status from the 30-minute time point. In total, the only very outer surface has experienced slight deterioration where only chocolate has fallen off. | No change in deterioration status from the 30-minute time point. In total, the only very outer surface has experienced slight deterioration where only chocolate has fallen off. | Completely deteriorated. Only sediment remains. | Completely deteriorated. | Completely deteriorated; only sediment remains. | Just as gel-like as the 30-minute time point, the wooden stirrer can still stand straight up without any support. |

As demonstrated by the data reported in Table 3, within the first 5 minutes (within the period before the first point of measure), the chocolate formulations are capable of protecting the psyllium contained therein better than formulations of comparator products which begin to deteriorate or absorb water quickly. As demonstrated, after 45 minutes of complete immersion in an aqueous environment, the milk chocolate and dark chocolate compositions of the invention experience far higher structural stability, and experience far less water absorption and product breakdown, than the comparison competitor fiber wafer and fiber powder supplement products.

EXEMPLARY ASPECTS OF THE INVENTION

The following is a non-limiting list of exemplary aspects of the invention, presented as a listing of embodiments, which is intended to highlight and illustrate various facets of the invention. In this respect, the invention provides, among other things—

In one aspect, the invention provides a flavored, lipid-rich, and psyllium fiber-containing nutritional composition useful in the management of appetite, regularity, and other dietary matters with improved consumer acceptability and compliance characteristics comprising in a non-extruded mixture comprising (a) at least 10 wt. % psyllium but no more than 18.5 wt. % psyllium and (b) saturated lipid in a concentration of between 17-20 wt. %; wherein the ratio of saturated lipid to psyllium is between 1:1-1.5:1; and further comprising (c) at least about 50 wt. % but no more than about 68 wt. % of a chocolate component ("chocolate"); (d) at least about 5 wt. %, such as about 5-15 wt. % of a texturizing element, optionally having a density of at least about 0.2 g/cm$^3$ (g/cc), such that the texturizing element is at least substantially homogeneously distributed throughout the composition; (e) between 10-15 wt. % unsaturated lipid; (f) a total amount of lipid of at least 28 wt. %; and (g) optionally no detectable amount of water (aspect 1).

In one aspect, the invention provides a composition such as that described in aspect 1, wherein the chocolate is selected from the group consisting of a chocolate which meets the United States Food and Drug Administration (US FDA) standard for milk chocolate, a chocolate which meets the US FDA standard for white chocolate, or a chocolate having no milk solids added (e.g., a dark chocolate) (aspect 2).

In one aspect, the invention provides a nutritional composition such as that described in any one of aspects 1 or 2, wherein the ratio of chocolate to psyllium is greater than 3:1 (aspect 3).

In one aspect, the invention provides a nutritional composition such as that described in any one of aspects 1-3, wherein the composition is at least substantially homogeneous (aspect 4).

In one aspect, the invention provides a nutritional composition such as that described in any one of aspects 1-4, wherein the psyllium of the composition does not absorb more than 20% of its water holding capacity during mastication and swallowing (aspect 5).

In one aspect, the invention provides a nutritional composition such as that described in any one of aspects 1-5, wherein at least 80% of the psyllium of the composition has a mesh size of at least 33 (aspect 6).

In one aspect, the invention provides a nutritional composition such as that described in any one of aspects 1-6, wherein the concentration of saturated lipid is between 17-19% (aspect 7).

In one aspect, the invention provides a nutritional composition such as that described in any one of aspects 1-7, wherein the concentration of unsaturated lipid in the composition is between 11-14 wt. % (aspect 8).

In one aspect, the invention provides a nutritional composition such as that described in any one of aspects 1-8, wherein the composition comprises at least 12 wt. % psyllium and no more than 17 wt. % psyllium (aspect 9).

In one aspect, the invention provides a nutritional composition such as that described in any one of aspects 1-9, wherein the nutritional composition is free of inulin (aspect 10).

In one aspect, the invention provides a nutritional composition such as that described in any one of aspects 1-10, wherein the psyllium is the only fiber ingredient in the composition contributing more than 10% of the total dietary fiber content of the composition to the composition (aspect 11).

In one aspect, the invention provides a nutritional composition such as that described in any one of aspects 1-11, wherein the composition is composed of from between about 5 wt. % and about 9 wt. % of lipid-rich ingredients that are solid at room temperature, excluding any solid lipid (fat) contained in the chocolate (aspect 12).

In another aspect, the invention provides a nutritional composition such as that described in aspect 12, wherein at least about 30% of the contribution of lipid-rich ingredient(s) that is/are solid at room temperature, excluding any solid lipid (fat) contained in the chocolate, is composed of unsaturated lipid (aspect 13).

In another aspect, the invention provides a nutritional composition such as that described in aspect 13, wherein the solid lipid (fat) is at least sizably, at least predominately, or at least substantially derived from cocoa butter (aspect 14).

In another aspect, the invention provides a nutritional composition such as that described in any one of aspects 1-14, wherein the nutritional composition lacks any coating, is free of any chocolate flavoring other than the chocolate, or both (aspect 15).

In another aspect, the invention provides a nutritional composition such as that described in any one of aspects 1-15, wherein an emulsion component is created by mixing two or more components together prior to addition to the remainder of the composition, the emulsion component added to the remainder of the composition as a single ingredient (aspect 16).

In another aspect, the invention provides a nutritional composition such as that described in aspect 16, wherein the emulsion component does not comprise chocolate, a texturizing component, psyllium, or cocoa butter (aspect 17).

In another aspect, the invention provides a nutritional composition such as that described in aspect 17, wherein the emulsion component comprises less than 0.2 wt. % lecithin (aspect 18).

In another aspect, the invention provides a nutritional composition such as that described in any of (aspects 16-18), wherein the emulsion component makes up less than about 30 wt. % of the nutritional composition (aspect 19).

In one aspect, the invention provides a flavored, lipid- and fiber-rich nutritional composition useful in the management of appetite, regularity, and other dietary matters comprising (a) at least 10 wt. % psyllium; (b) saturated lipid in a concentration of between 17-20 wt. %; (c) at least about 50 wt. % chocolate; (d) at least about 5% of a texturizing element, wherein the texturizing element has a density such that the texturizing element is at least substantially homogeneously distributed throughout the bar; (e) optionally less than 2.1 wt. % of any lipid-rich ingredient that is in liquid form at room temperature (i.e., an oil) outside of any such ingredient which may be present as part of the chocolate of (c); (f) and a total unsaturated lipid concentration ranging from between 10-15 wt. %, wherein the ratio of saturated lipid to psyllium is greater than 1.1:1 and the ratio of total lipid to psyllium is between 1.5:1 and about 3.5:1; and (g) no detectable amount of water (aspect 20).

In a further aspect, the invention provides a nutritional composition such as that described in aspect 20, wherein the chocolate is selected from the group consisting of a chocolate which meets the United States Food and Drug Administration (US FDA) standard for milk chocolate, a chocolate which meets the US FDA standard for white chocolate, or a chocolate having no milk solids added (e.g., a dark chocolate) (aspect 21).

In a further aspect, the invention provides a nutritional composition such as that described in any one of aspects 20-21, wherein the ratio of chocolate to psyllium is between 2-5:1 (aspect 22).

In a further aspect, the invention provides a nutritional composition such as that described in any one of aspects 20-22, wherein at least 80% of the psyllium of the composition has a mesh size of at least 33 (aspect 23).

In a further aspect, the invention provides a nutritional composition such as that described in any one of aspects 20-23, wherein the psyllium of the composition does not absorb more than 20% of its water holding capacity during mastication and swallowing (aspect 24).

In a further aspect, the invention provides a nutritional composition such as that described in aspect 24, wherein the psyllium of the composition does not absorb more than about 10% of its water holding capacity during consumption (aspect 25).

In a further aspect, the invention provides a nutritional composition such as that described in any one of aspects 20-25, wherein the texturizing element is a crisp rice having a density of at least about 0.2 g/cm3 (g/cc) (aspect 26).

In a further aspect, the invention provides a nutritional composition such as that described in any one of aspects 20-26, wherein upon mastication, the psyllium of the composition does not absorb sufficient water to cause gelation of the psyllium in the mouth of the consumer prior to swallowing to cause a report of a negative organoleptic experience (e.g., a negative mouth feel) to be reported by more than 50% of consumers who consume the nutritional composition (aspect 27).

In a further aspect, the invention provides a nutritional composition such as that described in any one of aspects 20-27, wherein the nutritional composition is a single-serving bar which does not comprise a coating (aspect 28).

In a further aspect, the invention provides a nutritional composition such as that described in any one of aspects 20-28, wherein the maximum amount of psyllium in the composition is 19 wt. %, 18.5 wt. %, or 18 wt. % (aspect 29).

In a further aspect, the invention provides a nutritional composition such as that described in any one of aspects 20-29, wherein the bar contains greater than about 3 g, preferably greater than about 3.1 g or 3.2 g, of psyllium per labeled serving size (aspect 30).

In a further aspect, the invention provides a nutritional composition such as that described in any one of aspects 20-30, wherein the maximum amount of saturated lipid is 20 wt. % (aspect 31).

In a further aspect, the invention provides a nutritional composition such as that described in any one of aspects 20-31, wherein the majority of saturated lipid in the composition not contributed by a chocolate ingredient is derived from cocoa butter (aspect 32).

In a further aspect, the invention provides a nutritional composition such as that described in any one of aspects 20-32, wherein the ratio of chocolate to psyllium is at least 3:1 (aspect 33).

In a further aspect, the invention provides a nutritional composition such as that described in any one of aspects 20-33, wherein the ratio of saturated lipid to psyllium is between 1.1-1.5:1 (aspect 34).

In a further aspect, the invention provides a nutritional composition such as that described in any one of aspects 20-34, wherein the ratio of chocolate:psyllium:saturated lipid is approximately 3.7-5.2:1:1-1.5 (aspect 35).

In a further aspect, the invention provides a nutritional composition such as that described in any one of aspects 20-35, wherein the texturizing agent is present in an amount of at least 7 wt. %, and optionally wherein most or all the texturizing element is a crisp rice (aspect 36).

In a further aspect, the invention provides a nutritional composition such as that described in aspect 36, wherein the nutritional composition comprises crisp rice and the crisp rice is present in an amount of at least 7% (aspect 37).

In a further aspect, the invention provides a nutritional composition such as that described in any one of aspects 20-37, wherein the viscosity of the final composition, when being deposited during manufacturing, is at least 20% less than the viscosity of a similar composition having a lower percent saturated lipid by weight, a higher amount of lecithin by weight, or both (aspect 38).

In a further aspect, the invention provides a nutritional composition such as that described in any one of aspects 20-38, wherein the frequency of choking, coughing, gagging, or inability to swallow related to ingestion of a high-fiber product is reduced by at least 5% as measured by a consumer testing panel comprising at least 20 participants or an otherwise appropriately powered consumer preference study (aspect 39).

In a further aspect, the invention provides a nutritional composition such as that described in any one of aspects 20-39, wherein the amount of lecithin in the composition is less than 1%, preferably less than about 0.5 wt. %, more preferably less than about 0.25 wt. % (aspect 40).

In a further aspect, the invention provides a nutritional composition such as that described in any one of aspects 20-40, wherein the composition meets the United States Food and Drug Administration guidelines for being capable of being labeled as "sugar-free" (aspect 41).

In a further aspect, the invention provides a nutritional composition such as that described in any one of aspects 20-41, wherein the composition comprises a crispy protein as the texturizing element in addition to, or instead of, a crispy rice (aspect 42).

In a further aspect, the invention provides a nutritional composition such as that described in any one of aspects 20-42, wherein in an appropriately powered consumer preference survey or in a consumer preference survey of at least 20 people, at least 10%, preferably at least 25%, of consumers tested demonstrate a preference for consumption of the nutritional composition over that of one or more reference high-fiber dietary supplement(s) (aspect 43).

In a further aspect, the invention provides a nutritional composition such as that described in any one of aspects 20-43, wherein the composition does not comprise any one or more of the following ingredients: inulin, almonds, xylose, sugar alcohols (e.g., sorbitol), wheat dextrin, hydrolyzed starch oligosaccharide, monosaccharide, disaccharide, polyglucose, polymaltose, maltodextrin, glycerin(e), peanut butter, humectants, leavening agent, pectin, guar gum, senna, oat, pectin, chia seeds, fruit, algae or seaweed, carrageenan, tocopherols, alginates, other algae-derived products, maltodextrin, lactitol, cholestyramine, resistant or hydrolyzed starch, polyester, caffeic acid, chlorogenic acid, ferulic acid, xanthan gum, HPMC/HPC, arabinose, cyclodextrin, caramel, antibodies, confectionary sugar, preservatives, corn fiber, wheat fiber, beta-glucan, probiotics/prebiotics, polyethylene glycol (PEG), a sterol-based component, a stanol-based component, and erythritol (aspect 44).

In a further aspect, the invention provides a nutritional composition such as that described in any one of aspects 20-44, wherein the nutritional composition contains no more than about 2.1 wt. % of any lipid that would be a liquid at room temperature (an oil) outside of any such lipid in the chocolate ingredient (aspect 45).

In a further aspect, the invention provides a nutritional composition such as that described in any one of aspects 20-45, wherein the nutritional composition is free from one or more of safflower oil, sunflower oil, sesame oil, walnut oil, olive oil, flaxseed oil, chia seed oil, almond oil, corn oil, grape seed oil, peanut oil, other nut oils, and combinations thereof (aspect 46).

In a further aspect, the invention provides a nutritional composition such as that described in any one of aspects 20-46, wherein the total amount of lecithin added by ingredients other than the chocolate in the composition is less than about 0.15 wt. % (aspect 47).

In a further aspect, the invention provides a nutritional composition such as that described in aspect 47, wherein the total amount of lecithin added by ingredients other than the chocolate in the composition is between about 0.05 wt. % and 0.15 wt. % (aspect 48).

In a further aspect, the invention provides a nutritional composition such as that described in aspect 48, wherein the total amount of lecithin added by any ingredients other than chocolate is between about 0.05 wt. % and 0.1 wt. % (aspect 49).

In a further aspect, the invention provides a nutritional composition such as that described in any one of aspects 20-49, wherein an emulsion component is created by mixing two or more components together prior to addition to the remainder of the composition, the emulsion component added to the remainder of the composition as a single ingredient (aspect 50).

In a further aspect, the invention provides a nutritional composition such as that described in aspect 50, wherein the emulsion component does not comprise chocolate, a texturizing component, psyllium, or cocoa butter (aspect 51).

In a further aspect, the invention provides a nutritional composition such as that described in aspect 51, wherein the emulsion component comprises less than 0.2 wt. % lecithin (aspect 52).

In a further aspect, the invention provides a nutritional composition such as that described in any one of aspects 50-52, wherein the emulsion component makes up less than about 30% of the nutritional composition (aspect 53).

In a further aspect, the invention provides a method of suppressing appetite, regulating digestive regularity, easing constipation, or otherwise regulating health by modifying the diet in an individual comprising the individual consuming about 10 g-about 100 g, such as 12 g-96 g, of the nutritional composition described in any one of aspects 1-53 per day for one or more days (aspect 54).

In an additional aspect, the invention provides a nutritional composition such as that described in aspect 54, wherein the about 10 g-about 100 g, e.g., the 12 g-96 g, of the nutritional composition represents between one half to four servings of the nutritional composition (aspect 55).

In one aspect, the invention provides a nutritional composition such as that described in aspect 55, wherein the nutritional composition in the form of a pocket-sized snack bar or meal bar (aspect 56).

In one aspect, the invention provides a method of suppressing appetite, comprising ingesting the nutritional composition such as that described in aspects 1-53 at an interval before or with at least one meal to suppress appetite and facilitate a reduction of total caloric intake throughout a 24-hour period (aspect 57).

In one aspect, the invention provides a method of suppressing appetite in an individual, the method comprising the individual consuming a nutritional composition comprising (a) at least ten wt. % psyllium; (b) saturated lipid in a concentration of between 17-21 wt. %; (c) at least about 50 wt. % chocolate; (d) at least about 5% of a texturizing element, wherein the texturizing element has a density such that the texturizing element is homogeneously distributed throughout the bar; (e) less than 2.1 wt. % of a lipid-rich ingredient that is in liquid form at room temperature (an oil) outside of any chocolate component; (f) unsaturated lipid in a concentration ranging from between 10-15 wt. %, wherein the ratio of saturated lipid to psyllium is between 1.1:1 and 2:1 and the ratio of total lipid to psyllium is between 1.5:1 and about 3.5:1; and (g) no detectable amount of water (aspect 58).

In one aspect, the invention provides a method of delivering a safe and effective amount of fiber supplement to a consumer comprising (I) administering to the consumer a composition comprising (a) at least ten wt. % psyllium; (b) saturated lipid in a concentration of between 17-21 wt. %; (c) at least about 50 wt. % chocolate; (d) at least about 5% of a texturizing element, wherein the texturizing element has a density such that the texturizing element is homogeneously distributed throughout the bar; (e) less than 2.1 wt. % total lipid-rich ingredient in liquid form at room temperature (i.e., an oil) outside of any chocolate component; (f) and an unsaturated lipid in a concentration ranging from between 10-15 wt. %, wherein the ratio of saturated lipid to psyllium is between 1.1:1 and 2:1 and the ratio of total lipid to psyllium is between 1.5:1 and about 3.5:1; and (g) no detectable amount of water; and (II) causing the consumer to consume each unit dose in a ratio with water of no less than 1-unit dose (serving size): 16 oz of water for the first week of fiber supplementation; and (III) optionally causing the consumer to decrease the ratio of nutritional product consumption to minimum associated water consumption to as low as 1-unit dose: 5.3 oz of water for each subsequent week of fiber supplementation (aspect 59).

In one aspect, the invention provides a method of delivering a safe and effective amount of fiber supplement to a consumer comprising providing to the consumer from about 1-unit dose to about 4-unit doses of a non-extruded, homogeneous composition comprising (a) at least ten wt. % psyllium; (b) saturated lipid in a concentration of between 17-21 wt. %; (c) at least about 50 wt. % chocolate; (d) at least about 5% of a texturizing element, wherein the texturizing element has a density such that the texturizing element is homogeneously distributed throughout the bar; (e) less than 2.1 wt. % total lipid in liquid form at room temperature (i.e., an oil) outside of any chocolate component; (f) and an unsaturated lipid in a concentration ranging from between 10-15 wt. %, wherein the ratio of saturated lipid to psyllium is between 1.1:1 and 2:1 and the ratio of total lipid to psyllium is between 1.5:1 and about 3.5:1; and (g) no detectable amount of water, without instructing the consumer to consume the composition with any suggested amount of water (aspect 60).

In one aspect, the invention provides a method of reducing caloric intake in an individual, the method comprising (a) administering to the individual approximately 10 g to approximately 100 g, e.g., 12 g-96 g, of the nutritional composition of any one of aspects 1-46 per day for a set period; (b) monitoring the caloric intake of the individual throughout the set period of time; and (c) adjusting the amount of nutritional composition administered to the individual per day after the set period of time up or down according to a targeted daily caloric intake goal of the individual (aspect 61).

In one aspect, the invention provides a method such as that described in aspect 61, wherein the method is repeated two or more times until an optimal daily amount of nutritional composition is established that meets the targeted daily caloric intake goals of the individual, and wherein, upon establishing the optimal amount of nutritional composition to be consumed daily, the individual continues to consume the established amount of nutritional composition daily to maintain the targeted caloric intake goal (aspect 62).

In one aspect, the invention provides a method of regulating digestive regularity in an individual, the method comprising (a) administering to the individual approximately 10 g to approximately 100 g, e.g., 12 g-96 g, of the nutritional composition described in any one of aspects 1-46 per day for a set period; (b) monitoring the digestive regularity of the individual throughout the set period of time; and (c) adjusting the amount of nutritional composition administered to the individual per day after the set period of time up or down according to a targeted digestive regularity goal of the individual (aspect 63).

In one aspect, the invention provides a method such as that described in aspect 63, wherein the method is repeated two or more times until an optimal daily amount of nutritional composition is established that meets the targeted digestive regularity goal of the individual, and wherein, upon establishing the optimal amount of nutritional composition to be consumed daily, the individual continues to consume the established amount of nutritional composition daily to maintain the targeted digestive regularity goal (aspect 64).

In one aspect, the invention provides a method of regulating nutritional intake in an individual having a predisposition for the consumption of non-nutritious snacks, wherein the method comprises administering the nutritional composition such as that described in any one of aspects 1-51 to the individual as part of a professionally managed diet program (aspect 65).

In one aspect, the invention provides a method such as that described in aspect 65, wherein the individual is an individual that previously has been recommended or prescribed a psyllium supplemented diet and found maintaining compliance with the prior psyllium-rich diet to be difficult, ceased the prior psyllium-rich diet, or both (aspect 66).

In one aspect, the invention provides a method of supplementing the diet of an individual with a safe and effective amount of fiber comprising providing an individual 10-100 g of a nutritional composition comprising (a) at least ten wt. % psyllium and (b) saturated lipid in a concentration of greater than or equal to about 18%, wherein the ratio of saturated lipid to psyllium is greater than 1.1:1; and further comprises (c) at least 50 wt. % of a chocolate composition; (d) at least 5 wt. % of a crisp grain wherein the crisp grain has a density such that the crisp grain is at least substantially homogeneously distributed throughout the composition; (e) between 10 and 15 wt. % unsaturated lipid; and (f) no detectable amount of water (aspect 67).

In one aspect, the invention provides a method such as that described in aspect 67, wherein 12-96 g of the nutritional composition represents between one half to four servings (aspect 68).

In one aspect, the invention provides a method such as that described in any one of aspects 67-68, wherein the nutritional composition comprises greater than 3 g, preferably greater than 3.1 g or greater than 3.2 g of psyllium per labeled serving in packaged form (aspect 69).

In one aspect, the invention provides a method such as that described in any one of aspects 67-69, wherein the method reduces the caloric intake of the individual when the nutritional composition is consumed as part of a caloric intake reduction program (aspect 70).

In one aspect, the invention provides a method such as that described in aspect 70, wherein the caloric intake control program comprises administering to the individual the nutritional composition at least once per day for a set period, monitoring the caloric intake of the individual throughout the set period; and adjusting the amount of nutritional composition administered to the individual per day after the set period up or down according to a targeted daily caloric intake goal of the individual (aspect 71).

In one aspect, the invention provides a method such as that described in aspect 71, wherein the method is repeated two or more times until an optimal daily caloric intake is established that meets the targeted caloric intake goal of the individual, and wherein, upon establishing the optimal amount of nutritional composition to be consumed daily, the individual continues to consume the established amount of nutritional composition daily to maintain the targeted caloric intake goal (aspect 72).

In one aspect, the invention provides a method such as that described in any one of aspects 67-72, wherein the method regulates digestive regularity when the nutritional composition is consumed as part of a regularity control program (aspect 73).

In one aspect, the invention provides a method such as that described in aspect 73, wherein the regularity control regimen comprises administering the individual the nutritional composition at least once per day for a set period of time, monitoring the digestive regularity of the individual throughout the set period of time, and adjusting the amount of nutritional composition administered to the individual per day after the set period of time up or down according to a targeted digestive regularity goal of the individual (aspect 74).

In one aspect, the invention provides a method such as that described in aspect 74, wherein the method is repeated two or more times until a target daily amount of nutritional composition is established that meets the targeted digestive regularity goal of the individual, and wherein, upon establishing the optimal amount of nutritional composition to be consumed daily, the individual continues to consume the established amount of nutritional composition daily to maintain the targeted digestive regularity goal (aspect 75).

In one aspect, the invention provides a method such as that described in any one of aspects 67-75, wherein the nutritional composition is in the form of a pocket-sized snack bar or meal bar (aspect 76).

In one aspect, the invention provides a method such as that described in any one of aspects 67-76, wherein the nutritional composition comprises less than about 0.25 wt. % lecithin (aspect 77).

In one aspect, the invention provides a nutritional composition such as that described in any one of aspects 1-53, wherein (a) the total lipid in a single serving represents between about 8-14 percent Daily Value of total fat, (b) the total saturated fat represents between about 18-22 percent Daily Value of total saturated fat, or (c) both (a) and (b) are true (aspect 78).

In one aspect, the invention provides a nutritional composition such as that described in aspect 78, wherein (a) the total lipid in a single serving represents between about 10-12 percent Daily Value of total fat, (b) the total saturated fat represents about 20 percent Daily Value of total saturated fat, or (c) both (a) and (b) are true (aspect 79).

In one aspect, the invention provides a nutritional composition such as that described in any one of aspects 1-53 and 78-79, wherein the amount of lipid contributing to the total lipid in the composition which is contributed to that total by ingredients other than the chocolate component (e.g., is contributed by the lipid component) is greater than 8 wt. % (aspect 80).

In one aspect, the invention provides a nutritional composition such as that described in aspect 80, wherein the amount of lipid contributed to the total lipid in the composition which is contributed to that total by ingredients other than the chocolate component (e.g., is contributed by the lipid component) is greater than 9% (aspect 81).

In one aspect, the invention provides a nutritional composition such as that described in any one of aspects 1-53 or 78-81, wherein the ratio of the wt. % of the composition represented by the chocolate component to the wt. % of the total saturated lipid content of the composition is greater than 2:1 (aspect 82).

In one aspect, the invention provides a nutritional composition such as that described in aspect 82, wherein the wt. % of the composition represented by the chocolate component to the wt. % of the total saturated lipid content of the composition is greater than 2.5:1 (aspect 83).

In one aspect, the invention provides a nutritional composition such as that described in aspect 83, wherein the wt. % of the composition represented by the chocolate component to the wt. % of the total saturated lipid content of the composition is greater than 3:1 (aspect 84).

In one aspect, the invention provides a nutritional composition such as that described in any of aspects 1-53 or 78-84, wherein the chocolate lipid:total lipid:lipid component lipid ratio is about 1-3:2-4:1 (aspect 85).

In one aspect, the invention provides a nutritional composition such as described in aspect 85, wherein the chocolate lipid:total lipid:lipid component lipid ratio is about 2:3:1 (aspect 86).

In one aspect, the invention provides a nutritional composition such as described in any one of aspects 1-53 or 78-86, wherein the ratio of the lipid component lipid:total lipid ratio is about 1:3-4 (aspect 87).

In one aspect, the invention provides a nutritional composition such as described in any one of aspects 1-53, or 78-87, wherein the ratio of saturated lipid to unsaturated lipid is greater than 1:1 (aspect 88).

In one aspect, the invention provides a nutritional composition such as described in aspect 88, wherein the ratio of saturated lipid to unsaturated lipid is less than 2:1 (aspect 89).

In one aspect, the invention provides a nutritional composition such as described in any one of aspects 1-53 or 78-89, wherein the ratio of total lipid to total saturated lipid is about 1:1.4-2.4 (aspect 90).

In one aspect, the invention provides a nutritional composition such as described in any one of aspects 1-53 or 78-90, wherein a 24 g serving comprises between about 105 and 115 calories (aspect 91).

In one aspect, the invention provides a nutritional composition such as described in aspect 91, wherein a 24 g serving comprises about 110 calories (kilocalories/food calories) (aspect 92).

In an additional aspect, the invention provides a method of supplementing the amount of dietary fiber in a person's diet comprising (1) administering to the person 1 unit of a psyllium-containing nutritional composition per day with about 8 ounces of water for a period of about 1 week and (2) thereafter administering to the person 1-2 units of the psyllium-containing composition 1-3 times per day, each time with about 8 ounces of water, each unit of the psyllium-containing composition comprising (a) psyllium in an amount that provides 5%-8.5% of the Percent Daily Value (PDV) of dietary fiber, at least 50% of the psyllium having an average mesh size of at least 33; (b) a chocolate component that makes up 55-75 wt. % of the composition and contributes part of the total lipid content of the composition; (c) a lipid component that contributes part of the total lipid content of the composition and is made of one or more lipids that are separate from the chocolate component, the ratio of total lipid contributed by the chocolate component to the total lipid contributed by the lipid component being between 1.25:1 and 2.75:1, the total lipids providing between 3.5-7.5% of the PDV for total fat and between 7.5-12.5% of the PDV for saturated fat; and (d) a non-psyllium texturizing component that makes up at least 5 wt. % of the composition, wherein the PDV is the United States Food and Drug Administration percent Daily Value for the indicated nutritional component based on a 2,000 calorie-per-day diet (aspect 93).

In another aspect, the invention provides a method such as that described in aspect 93, wherein each unit of the composition comprises about 35-70 calories (aspect 94).

In another aspect, the invention provides a method such as that described in aspect 94, wherein the ratio of total lipid contributed by the chocolate component to the lipid component being between 1.75:1 and 2.75:1 (aspect 95).

In another aspect, the invention provides a method such as that described in aspect 95, wherein the texturizing component is primarily composed of a crisp rice ingredient having a density of at least 0.2 g per cubic centimeter (aspect 96).

In another aspect, the invention provides a method such as that described in aspect 96, wherein the psyllium makes up at least about 90% of the soluble dietary fiber of the composition (aspect 97).

In another aspect, the invention provides a method such as that described in aspect 97, wherein the composition is free of inulin (aspect 98).

In another aspect, the invention provides a method such as that described in any one of aspects 93-98, wherein the method further comprises the features of the aspects described in any one of aspects 54-77 (aspect 99).

In another aspect, the invention provides the method of aspect 99, wherein the nutritional composition resulting from the method has the features of the aspects described in any one of aspects 1-53 or any one of aspects 78-92 (aspect 100).

In a further aspect, a method of supplementing the amount of dietary fiber in a person's diet comprising administering a daily amount of a psyllium-containing nutritional composition to the person, the nutritional composition being composed of psyllium, a chocolate component, a non-chocolate lipid component, and a non-psyllium texturizing component, wherein the nutritional composition is prepared from ingredients comprising (a) psyllium in an amount equivalent to between about 6% and 48% of the Percent Daily Value (PDV) of dietary fiber, at least 50% of the psyllium having an average mesh size of at least 33; (b) a chocolate component that accounts for 55-70 wt. % of the composition; (c) a lipid component comprising one or more lipids that are separate from the chocolate component, (d) a total lipid content comprising lipids from the chocolate component and lipid component, the ratio of total lipid contributed by the chocolate component to total lipid contributed by the lipid component being between 1.5:1 and 3:1, the total lipids providing 4-42% of the PDV for total fat and 8-72% of the PDV for saturated fats; and (e) a non-psyllium texturizing component that makes up at least 5 wt. % of the composition, wherein the PDV is equivalent to the United States Food and Drug Administration Percent Daily Value for the indicated nutritional component based on a 2,000 calorie-per-day diet (aspect 101).

In a further aspect, the invention provides a method such as that described in aspect 101, wherein consuming the composition provides about 40-420 calories to the person per day (aspect 102).

In a further aspect, the invention provides a method such as that described in any one of aspects 101 or 102, wherein the ratio of total lipid contributed by the chocolate component to the total lipid contributed by the lipid component being between 1.75:1 and about 2.5:1 (aspect 103).

In a further aspect, the invention provides a method such as that described in any one of aspects 101-103, wherein the texturizing component is primarily composed of a crisp rice ingredient having a density of at least 0.2 g per cubic centimeter (aspect 104).

In a further aspect, the invention provides a method such as that described in any one of aspects 101-104, wherein the method further comprises performing any one of the steps of aspects described in any one of aspects 54-77 (aspect 105).

In another aspect, the invention provides a method such as that described in aspect 105, wherein the nutritional composition has the features of any one of aspects 1-53 or 78-92 (aspect 106).

In a further aspect, the invention provides a psyllium-containing nutritional composition useful in the management of appetite, regularity, and other dietary fiber-related health matters, prepared by a process comprising the steps of (a) establishing an emulsion comprising (i) coconut oil in an about of about 0.8-0.95 wt. % of the composition; (ii) a vegetable oil in an amount of about 1.5-2.3 wt. % of the composition; (iii) a starch in an amount of about 3-6 wt. % of the composition; and (iv) an emulsifier in an amount of about 0.075-0.125 wt. % of the composition; and (b) blending the emulsion as an ingredient with other ingredients comprising (i) psyllium in an amount equivalent to 10 wt. %-18.5 wt. % of the total composition; (ii) a chocolate component in an amount equivalent to 55 wt. %-67.5 wt. % of the total composition; (iii) a non-emulsion lipid component that is separate from the chocolate component in an amount equivalent to 5 wt. %-10 wt. % of the total composition; and (iv) a non-psyllium texturizing element in an amount equivalent to 5 wt. %-15 wt. % of the total composition, such that the final composition comprises between 16 wt. %-20 wt. % saturated lipid, 11 wt. %-15 wt. % unsaturated lipid; and at least 30 wt. % total lipids (aspect 107).

In an additional aspect, the invention provides a composition such as that described in aspect 107, wherein the ratio of lipids contributed by the chocolate component-to-lipids contributed by the combination of lipids of the emulsion component and the non-emulsion lipid component is between 1.25:1-2.75:1 (aspect 108).

In an additional aspect, the invention provides a composition such as that described in any one of aspects 107 or 108, wherein the emulsifier is a lecithin (aspect 109).

In an additional aspect, the invention provides a composition such as described in any one of aspects 107-109, wherein the vegetable oil at least primarily comprises canola oil (aspect 110).

In an additional aspect, the invention provides a composition such as described in any one of aspects 107-110, wherein the starch at least primarily comprises corn starch (aspect 111).

In an additional aspect, the invention provides a composition such as described in any one of aspects 107-111, wherein the composition is a non-extruded composition (aspect 112).

In an additional aspect, the invention provides a composition such as described in any one of aspects 107-112, wherein the composition has the features of the aspects described in any one of aspects 1-53 (aspect 113).

In a further aspect, the invention provides a psyllium-containing nutritional composition made of ingredients comprising (a) psyllium in an amount equivalent to 10 wt. %-18 wt. % of the total composition and making up at least 90% of the total fiber in the composition; (b) 55 wt. %-67.5 wt. % of a chocolate component; (c) a non-psyllium texturizing component in an amount equivalent to at least 5 wt. % of the total composition; (d) a non-chocolate lipid component comprising a saturated lipid portion in an amount equivalent to 4.5 wt. %-6 wt. % of the total composition; and (e) a total lipid content comprising lipids from the chocolate component and lipid component, the ratio of total lipid contributed by the chocolate component to total lipid contributed by the lipid component being between 1.5:1 and 3:1 (aspect 114).

In a further aspect, the invention provides a composition such as that described in aspect 114, wherein psyllium makes up at least 99% of the fiber in the composition and at least 50% of the psyllium has an average mesh size of at least 33 (aspect 115).

In a further aspect, the invention provides a composition such as that described in aspect 114 or 115, wherein the composition is a non-extruded, substantially homogenous composition, which is free of preservatives (aspect 116).

In a further aspect, the invention provides a composition such as that described in any one of aspects 114-116, wherein at least about 85% of non-psyllium texturizing component is composed of a single ingredient (aspect 117).

In a further aspect, the invention provides a composition such as that described in any one of aspects 1-53, 78-92, or 107-117, wherein (a) the ratio of chocolate component to psyllium is about 3.7-5.2:1; (b) the ratio of total lipid to psyllium is about 2.1-3:1; (c) the ratio of saturated fat to psyllium is about 1.1-1.44:1; (d) the ratio of the amount of lipid contributed to the composition by chocolate to the amount of lipid contributed to the composition by ingredients other than those in the chocolate component is about 2:1; (e) the ratio of total lipid to total saturated lipid is about 1.4-2.24:1; (f) the ratio of chocolate component to total saturated lipid is about 2.6-4.1:1; (g) the ratio of psyllium to texturizing element is about 2:1; or (h) any combination of (a)-(g) are true (aspect 118).

In a further aspect, the invention provides a composition such as that described in aspect 118, where the composition can be described by comprising at least two of the ratios (a)-(g) (aspect 119).

The invention claimed is:

1. A chocolate, non-baked, psyllium-containing nutritional composition useful for managing appetite, promoting regularity, controlling glucose, or reducing the risk of heart disease, stroke, obesity, or type-2 diabetes obtained by the process comprising the steps of: (a) making an emulsion comprising: (i) coconut oil in an amount of about 0.8-0.95 wt. % based upon the total composition; (ii) a vegetable oil in an amount of about 1.5-about 2.3 wt. % based upon the total composition; (iii) a starch in an amount of about 3-about 6 wt. % based upon the total composition; and (iv) an emulsifier in an amount of about 0.075-about 0.125 wt. % based upon the total composition; and (b) blending the emulsion with a combination of ingredients comprising: (i) psyllium in an amount of about 10 wt. %-18.5 wt. % based upon the total composition; (ii) a chocolate component in an amount of about 55 wt. %-about 67.5 wt. % based upon the total composition; (iii) a non-emulsion lipid component that is separate from the chocolate component in an amount of about 5 wt. %-about 10 wt. % based upon the total composition; and (iv) a non-psyllium texturizing element in an amount equivalent to about 5 wt. %-about 15 wt. % based upon the total composition, wherein the composition comprises between about 16 wt. %-about 20 wt. % saturated lipid, 11 wt. %-15 wt. % unsaturated lipid; and at least 30 wt. % total lipids based upon the total amount of the composition, and wherein the emulsion and blending the emulsion with the combination of ingredients to form the nutritional composition significantly reduces clogging in processing machines compared to a composition made by a process which lacks the steps of establishing the emulsion and mixing the emulsion with the combination of ingredients.

2. The composition of claim 1, wherein the ratio of lipids contributed by the chocolate component-to-lipids contributed by the combination of lipids of the emulsion component and the non-emulsion lipid component is between 1.25:1-2.75:1.

3. The composition of claim 2, wherein the emulsifier is a lecithin.

4. The composition of claim 3, wherein the vegetable oil primarily comprises canola oil.

5. The composition of claim 4, wherein the starch primarily comprises corn starch.

6. The composition of claim 5, wherein at least 70% of the dietary fiber of the composition is composed of psyllium and the ratio of psyllium having a mesh size of 33 or greater to psyllium present as whole husk is less than 1.5:1 and the ratio of psyllium present as whole husk to psyllium having a mesh size of 33 or greater is 20:1 or less.

7. The composition of claim 6, wherein the composition is a substantially homogeneous composition.

8. The composition of claim 7, wherein at least about 85% of the non-psyllium texturizing component contains a single ingredient.

9. The composition of claim 7, wherein the texturizing component is primarily composed of a crisp rice having a density of at least 0.2 g per cubic centimeter.

10. The composition of claim 8, wherein the composition is a non-extruded composition.

11. The composition of claim 10, wherein the composition is free of inulin.

* * * * *